US006358733B1

(12) United States Patent
Motwani et al.

(10) Patent No.: US 6,358,733 B1
(45) Date of Patent: Mar. 19, 2002

(54) EXPRESSION OF HETEROLOGOUS MULTI-DOMAIN PROTEINS IN YEAST

(75) Inventors: Nalini Motwani, West Bloomfield; Robert Blackburn, Warren, both of MI (US)

(73) Assignee: Apolife, Inc., Detroit, MI (US)

( * ) Notice: Subject to any disclaimer, the term of this patent is extended or adjusted under 35 U.S.C. 154(b) by 0 days.

(21) Appl. No.: 09/574,492

(22) Filed: May 19, 2000

(51) Int. Cl.$^7$ ........................ C12N 15/63; C07H 21/04; C12P 21/02
(52) U.S. Cl. .................... 435/320.1; 435/69.1; 536/23.1
(58) Field of Search ............................ 435/320.1, 69.1; 536/23.1

(56) References Cited

U.S. PATENT DOCUMENTS

| | | | |
|---|---|---|---|
| 4,775,622 A | 10/1988 | Hitzeman et al. ........... | 435/69.4 |
| 4,801,542 A | 1/1989 | Murray et al. ............. | 435/69.4 |
| 4,816,397 A | 3/1989 | Boss et al. ................. | 435/69.6 |
| 4,876,197 A | 10/1989 | Burke et al. ............. | 435/320.1 |
| 5,135,854 A * | 8/1992 | MacKay et al. ........... | 435/69.1 |
| 5,312,735 A * | 5/1994 | Fink et al. ................. | 435/69.1 |
| 5,648,254 A * | 7/1997 | Mulvihill et al. ........... | 435/217 |
| 5,827,693 A | 10/1998 | DeAngelo et al. ......... | 435/69.6 |
| 6,051,405 A * | 4/2000 | FitzGerald et al. ........ | 435/69.7 |

OTHER PUBLICATIONS

Owens et al. Journal of Applied Bacteriology 72(1):32–38 1992.*

Romanos et al. Yeast 8:423–488 1992.*

Sawa T, Wu J, Akaike T and Maeda H (2000). Tumor–targeting chemotherapy by a xanthine oxidase–polymer conjugate that generates oxygen–free radicals in tumor tissue. *Cancer Res.* 60:666–671.

Blackburn RV, Spitz DP, Liu X, Galoforo SS, Sim JE, Ridnour LA, Chen JC, Davis BH, Corry PM and Lee YJ (1999). Metabolic oxidative stress activates signal transduction and gene expression during glucose deprivation in human tumor cells. *Free Radic. Biol Med.* 26:419–430.

Metosh–Dickey CA, Mason RP and Winston GW (1998). Single electron reduction of xenobiotic compounds by glucose oxidase from *Apergillus niger. Free Radic. Biol. Med.* 24:155–160.

Russoniello C, Somasundaram C, Schlom J, Deo YM and Keler T (1998). Characterization of a novel bispecific antibody that mediates Fcγ receptor type I–dependent killing of tumor–associated glycoprotein–72–expressing tumor cells. *Clin. Cancer Res.* 4:2237–2243.

Shusta EV, Raines RT, Plückthun A and Wittrup KD (1998). Increasing the secretory capacity of *Saccharomyces cerevisiae* for production of single–chain antibody fragments. *Nature Biotech.* 16:773–777.

Vaughan TJ, Osbourn JK and Tempest PR (1998). Human antibodies by design. *Nature Biotech.* 16:535 (1998).

Kozlovsky N, Rudich A, Potashnik R, Ebina Y, Muramaki T and Bashan N (1997). Transcriptional activation of the Glut1 gene in response to oxidative stress in L6 myotubes. *J. Bio Chem.* 272:33367–33372.

Salazar JJ and Van Houten B (1997). Preferential mitochondrial DNA injury caused by glucose oxidase as a steady generator of hydrogen peroxide in human fibroblasts. *Mutat. Res.* 385:139–149.

Seaver SS (1997). Monoclonal antibodies: using new techniques to reduce development time. *Genet. Eng. News*, Jan. 15, p. 13.

Melton RG and Sherwood RF (1996). Antibody–enzyme conjugates for cancer therapy. *J. Natl. Cancer Inst.* 88:153–165.

Motwani N, Talarico T, Jain S, Bajwa W, Blackburn R, Nwosu V, Holland M, DeAngelo J, Privalle C and Keng T (1996). Production, purification and characterization of recombinant huma hemoglobin Rainier expressed in *Saccharomyces cerevisiae. Proteins Expressions and Purification* 8:447–455.

Odajima T, Onishi M, Hayama E, Motoji N, Momose Y and Shigematsu A (1996). Cytolysis of B 16 melanoma tumor cells mediated by the myeloperoxidase and lactoperoxidase systems. *Biol. Chem.* 377:689–693.

Ohno K, Levin B and Meruelo D (1996). Cell–specific, multidrug delivery system using streptavidin–protein A fusion protein. *Biochem. Mol. Med.* 58:227–233.

Reiter Y and Pastan I (1996). Antibody engineering of recombinant Fv immunotoxins for improved targeting of cancer: disulfide–stabilized Fv immunotoxins. *Clin. Cancer Res.* 2:245–252.

Samoszuk MK, Wimley WC and Nguyen V (1996). Eradication of interleukin 5–transfected J558L plasmacytomas in mice by hydrogen peroxide–generating Stealth liposomes. *Cancer Res.* 56:87–90.

(List continued on next page.)

*Primary Examiner*—Robert A. Schwartzman
*Assistant Examiner*—Katharine F Davis
(74) *Attorney, Agent, or Firm*—Baker Botts, LLP

(57) ABSTRACT

This invention demonstrates the utility of a yeast expression system for the expression of functional heterologous multi-domain proteins in yeast. The yeast expression system allows for the inclusion of a plurality of (up to three) modular expression cassettes which may encode multiple polypeptide chains of a heterologous multi-domain protein on a single plasmid (Twin Cassette). Because multiple polypeptide chains may be encoded for by the expression cassettes of the present invention in a single vector, the system can produce equivalent amounts of the multiple polypeptide chains, thereby enhancing the yield of a functional heterologous multi-domain protein. For example, functional monoclonal antibodies (MAbs) comprising a heavy chain and a light chain of an immunoglobulin (IgG), and functional immunotoxins comprising an antibody domain and an oxidase toxin may be produced using the Yeast expression system of the present invention. In addition, functional single chain antibodies, antibody fragments and chimeric antibodies may also be produced.

3 Claims, 22 Drawing Sheets

OTHER PUBLICATIONS

Figure 1:
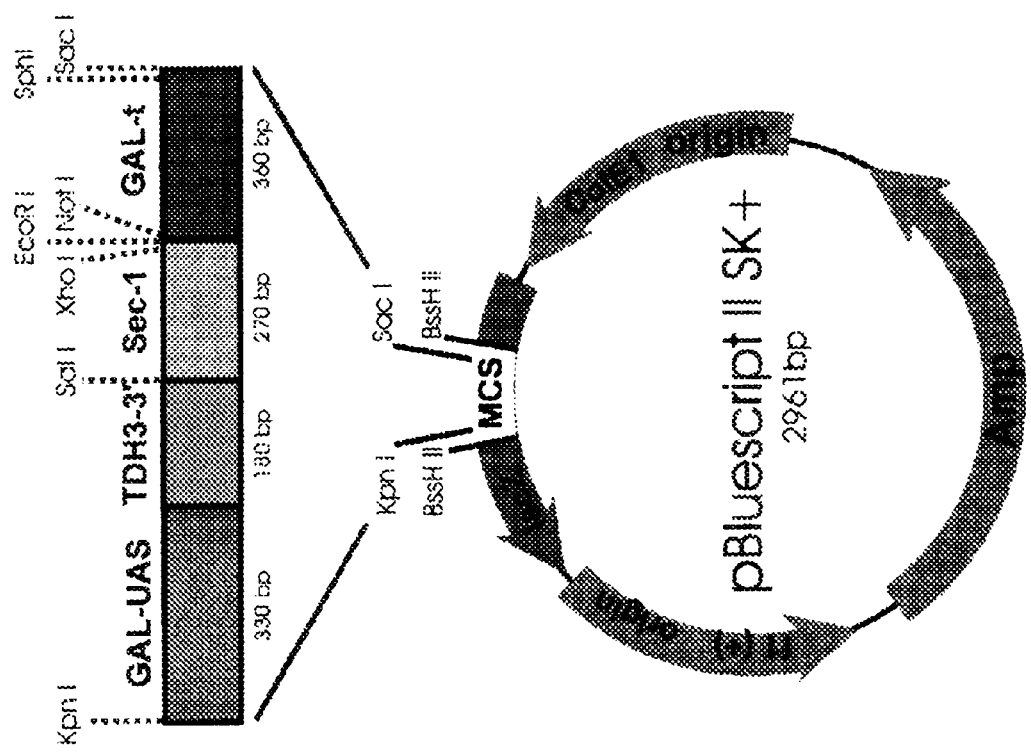

Hensing MCM, Rouwenhorst RJ, Heijnen JJ, van Dijken JP and Pronk JT (1995). Physiological and technological aspects of large–scale heterologous–protein production with yeasts. *Antoine Van Leeuwenhoek* 67:261–279.

Meixensberger J, Herting B, Roggendorf W and Reichmann H (1995). Metabolic patterns in malignant gliomas. *Neurooncol.* 24:153–161.

Ridder R, Schmitz R, Legay F and Gram H (1995). Generation of rabbit monoclonal antibody fragments from a combinatorial phage display library and their production in the yeast *Pichia pastoris. Biotechnology* 13:255–260.

Ben–Yoseph O and Ross BD (1994). Oxidation therapy: the use of a reactive oxygen species–generating enzyme system for tumour treatment. *Br. J. Cancer* 70:1131–1135.

De Leij L, Helrich W, Stein R and Mattes MJ (1994). SCLC–cluster–2 antibodies detect the pancarcinoma/epithelial glycoprotein EGP–2. *Int. J. Cancer Suppl.* 8:60–63.

Robinson DK, Chan CP, Yu Ip C, Tsai PK, Tung J, Seamans TC, Lenny AB, Lee DK, Irwin J and Silberklang M (1994). Characterization of a recombinant antibody produced in the course of a high yield batch–fed process. *Biotech Bioeng.* 55:783 (1997).

Samoszuk MK, Nguyen V, Thomas CT and Jacobson DM (1994). Effects of sonicated eosinophil on the in vitro sensitivity of human lymphoma cells to glucose oxidase. *Cancer Res.* 54:2650–2653.

Buckholz RG (1993). Yeast systems for the expression of heterologous gene products. *Curr. Opin Biotechnol.* 4:538–542.

Weiden PL, Breitz HB, Seiler CA, Bjorn MJ, Ratliff BA, Mallett R, Beaumier PL, Applebaum JW, Fritzberg AR and Salk D (1993). *J. Nucl. Med.* 34:2111–2119.

Bebbington CR, Renner G, Thomson S, King D, Abrams D and Yarranton GT (1992). High–level expression of a recombinant antibody from myeloma cells using a glutamine synthetase gene as an amplifiable selectable marker. *Biotechnol.* 10:169–175.

Brietz HB, Weiden PL, Vanderheyden J–L, Appelbaum JW, Bjorn MJ, Fer MF, Wolf SB, Ratliff BA, Seiler CA, Foisie DC, Fisher DR, Schroff RW, Fritzberg AR and Abrams PG (1992). Clinica experience with rhenium–186–labeled monoclonal antibodies for radioimmunotherapy: results of Phase I trials. *Nucl. Med.* 33:1099 (1992).

Buchner J, Pastan I and Brinkmann U (1992). A method for increasing the yield of properly folde recombinant fusion proteins: single–chain immunotoxins from renaturation of bacterial inclusion bodies. *Anal. Biochem.* 205:263–270.

Yu Ip C, Miller WJ, Kubeck DJ, Strang A–M, van Halbeek H, Piesecki SJ and Alhadeff JA (1992). Structural characterization of the N–glycans of a recombinant hepatitis B surface antigen derived from yeast. *Biochemistry* 31:285–295.

Nutter LM, Ngo EO, Fisher GR and Gutierrez PL (1992). DNA strand scission and free radical production in menadione–treated cells. *J. Biol. Chem.* 267:2472–2479.

Pietersz GA and McKenzie FC (1992). Antibody conjugates for the treatment of cancer. *Immunol Rev.* 129:57–80.

Bowdish, K, Tang Y, Hicks JB and Hilvert D (1991). Yeast expression of a catalytic antibody with chorismate mutase activity. *J. Biol. Chem.* 266:11901–11908.

Pastan I and Fitzgerald D (1991). Recombinant toxins for cancer treatment. *Science* 254:11731177.

Casentini–Borocz D and Bringman T (1990). Enzyme immunoconjugates utilizing glucose oxidas and myeloperoxidase are cytotoxic to *Candida tropicalis. Antimicrob. Agents and Chemoth.* 34:875–880.

Chouchane L, Bringman T, Barbier S, Traincard F and Strosberg AD (1990). Targeted killing of yeast expressing a HIV–1 peptide by antibody–conjugated glucose oxidase and horseradish peroxidase. *Immunology Letters* 25:359–366.

Frederick KR, Tung J, Emerick RS, Masiarz FR, Chamberlain SH, Vasavada A and Rosenberg S (1990). Glucose oxidase from *Aspergillu niger. J. Biol. Chem.* 265:3793–3802.

Glockshuber R, Malia M, Pfitzinger I and Plückthun A (1990). A comparison of strategies to stabilize Fv fragments. *Biochem.* 29:1362–1367.

Whittington H, Kerry–Williams S, Bidgood K, Dodsworth N, Peberdy J, Dobson M, Hinchliffe E and Ballance DJ (1990). Expression of the *Aspergillus niger* glucose oxidase gene in A. niger, A. nidulans and *Saccharomyces cerevisiae. Curr. Genet.* 18:531–536.

Sinha BK, Mimnaugh EG, Rajagopalan S and Myers CE (1989). Adriamycin activation and oxygen free radical formation in human breast tumor cells: protective role of glutathione peroxidase in adriamycin resistance. *Cancer Res.* 49:3844–3848.

Stanislawski M, Rousseau V, Goavec M and Ito H (1989). Immunotoxins containing glucose oxidase and lactoperoxidase with tumoricidal properties: in vitro killing effectiveness in a mouse plasmacytoma model. *Cancer Res.* 49:5497–5504.

Carlson JR (1988). A means of inducibly activating a cellular protein *Mol. Cell Biol.* 8:2638–2646.

Mavier P, Guigui B, Preaux A–M, Rosenbaum J, Lescs M–C, Zafrani ES and Dhumeaux D (1988) In vitro toxicity of hydrogen peroxide against normal vs. tumor rat hepatocytes: role of catalase and of the glutathione redox cycle. *Hepatology* 8:1673–1673.

Everse KE, Lin H, Stuyt EL, Brady JC, Buddingh F and Everse J (1985). Antitumour activity of peroxidases. *Br. J. Cancer* 51:743–746.

Starke PE and Farber JL (1985). Endogenous defenses against the cytotoxicity of hydrogen peroxide in cultured rat hepatocytes. *J. Biol. Chem.* 260:86–92.

Wood CR, Boss MA, Kenten JH, Calvert JE, Roberts NA and Emtage JS (1985). The synthesis and assembly of functional antibodies in yeast. *Nature* 314:446449.

Hitzeman RA, Hagie FE, Levine HL, Goeddel DV, Ammerer G and Hall BD (1981). Expression of a human gene for interferon in yeast. *Nature* 293:717–722.

Holland MJ, Holland JP and McAllister L (1981). Structure and expression of yeast glycolytic genes. *Basic Life Science* 19:291–303.

Pazur JH, Kleppe K and Cepure A (1965). A glycoprotein structure for glucose oxidase form *Aspergillus niger. Arch. Biochem. Biophys.* 111:351–357.

Warburg O (1956). On the origin of cancer cells. *Science* 123:309–317.

\* cited by examiner

| Transformants | OD$_{600}$ | | | |
|---|---|---|---|---|
| | YNB | YNB+phosphate | M.S.M. | M.S.M+Biotin |
| RgsApoFGt (scFv-SA) | 4.0 | 8.2 | 21.3 | 25.3 |
| pPM40 (control) | 9.2 | 17.8 | 29.0 | 35.0 |

Table I: <u>Comparison of Media for Growth of Yeast Strains.</u> Yeast transfected with the scFv-SA fusion protein expression vector (RGsApoFGt) or control plasmid (pPM40) were fermented in shake flasks with four different media compositions. The OD$_{600}$ of the transformants was determined after 72 hrs of fermentation. YNB- yeast nitrogen base, M.S.M.- minimal salt medium

FIG. 21

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
ttgagctccc cagaaataag gc                                        22

<210> SEQ ID NO 2
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 2
agaaggtttt tttagcccgg gca                                       23

<210> SEQ ID NO 3
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 3
cgatcggagc tcattaacgc ctttcgctca taa                            33

<210> SEQ ID NO 4
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 4
gtgtcctctc gtatctttac cccaaagatc tgcgcga                        37

<210> SEQ ID NO 5
<211> LENGTH: 29
<212> TYPE: DNA

```
<213> ORGANISM: Artificial Sequence
<220> FEATURE:
<223> OTHER INFORMATION: Synthetic Oligonucleotide

<400> SEQUENCE: 5
atcccgggaa ggttgaaacc agttccctg                                29

<210> SEQ ID NO 6
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 6
gtgtgtattt atttgtttta ccacgtgcgc                               30

<210> SEQ ID NO 7
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 7
ccggccgtct ctagatctgg ctttgatctt actatcattt gg                 42

<210> SEQ ID NO 8
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 8
gtattgtggt tcgttgatta tgatattgat agttattatt acgtgcacgg cg      52
```

EXPRESSION OF HETEROLOGOUS MULTI-DOMAIN PROTEINS IN YEAST

The present invention involves subject matter developed under National Institute of Health Grant Numbered 1R43AI40822-01, so that the United States Government may have certain rights herein.

1. INTRODUCTION

The invention is directed to a cost effective system for the production of heterologous recombinant proteins in yeast using a single vector to express functional multi-domain proteins, including proteins comprising multiple polypeptide chains. The proteins may include, but are not limited to, recombinant monoclonal antibodies, single antibody chains, chimeric antibodies, immunotoxins, etc. The vector of the present invention may comprise a plurality of modular expression cassettes which facilitate the manipulation of the expression of various subunits of a protein. The expression cassettes may additionally comprise a hybrid, constitutive, or inducible promoter, signal sequences for secretion of protein, nucleic acid encoding the protein of interest (e.g. a heavy and light chain of an antibody molecule) and a transcriptional termination sequence. Furthermore, the invention is directed to improved techniques to reduce development time for production of functional heterologous recombinant multi-domain proteins. The recombinant molecules produced by this invention are useful for research, diagnostic and/or therapeutic applications.

2. BACKGROUND OF THE INVENTION

2.1 MAb Expression

Monoclonal antibodies hold great promise for application in a wide range of diagnostic and therapeutic (clinical) settings, as evidenced by current clinical use of monoclonal antibody-derived products for transplantation, tumor imaging, therapeutics and diagnostics.

Currently two main methods used for commercial monoclonal antibody ("MAb") production are generally employed; in vivo mouse ascites fluid and in vitro cultivation of hybridoma cell lines. The production of a MAb in vivo from mouse ascites fluid is limited in that it produces solid tumors in mice and results in death of the animal and low-level yields of MAbs. In vitro cultivation of hybridoma cell lines also has limitations. For example, it has been estimated that a minimum of 1000 clones need to be screened to find just two MAb-producing hybridoma cell lines. Most clones are not considered to be useful because of inappropriate specificity. In addition, after going through several passages, hybridoma cell lines may lose certain chromosomes and stop producing the MAb. Recombinant production of MAbs could avoid some of the problems associated with production of MAbs from hybridoma cell lines and ascites fluid.

A large number of heterologous single chain polypeptides have been produced by host cells transformed by recombinant DNA techniques. However, very few functional multichain polypeptides have been successfully produced by recombinant techniques. Recombinant dimeric polypeptides have been synthesized as a single chain polypeptide, coded for by a single DNA sequence, which is then cleaved in the host cell subsequent to synthesis to form the dimeric structure. In some cases the polypeptide chains are synthesized separately and then assembled after isolation from the host cell. Disadvantages of recombinant protein production in *E. coli* include inefficient secretion, formation of insoluble protein complexes in inclusion bodies, the presence of endotoxin, lack of glycosylation, and lack of N-terminal methionine processing (see Buchner, *Anal. Biochem.* 205:263 (1992)), which often affect the functionality of the recombinant protein, or hinder efficient and cost-effective production and purification.

A number of heterologous proteins have been expressed in yeast. Examples include interferon (U.S. Pat. No. 4,775,622, Hitzeman, et al., Nature, 292, 717, 1991); platelet derived growth factor (U.S. Pat. No. 4,801,542); and glyceraldehyde-3-phosphate dehydrogenase (Holland et al., *Basic Life Science,* 19:291, (1981)). Burke et al., U.S. Pat. No. 4,876,197 discloses a DNA construct comprising a transcription regulatory region obtained from the yeast ADH2, the regulatory region of acid phosphatase (PHO5) or GAL4 which provides for inducible transcriptional regulation, a transcriptional initiation region from the yeast glyceraldehyde-3-phosphate dehydrogenase gene ("TDH3") and a terminator region.

The structure of antibody molecules and the nature of genes coding for them permit extensive manipulation and shuffling of antibody genes to produce recombinant antibodies with domains from different proteins and species. Such manipulation and shuffling can create MAbs with desired specificity, effector functions, reduced immunogenicity and/or binding sites for additional molecules. Recent advances in genetic engineering have made it possible to design and generate single chain, chimeric and humanized antibodies with desired specificities and binding sites (Vaughan et al., *Nature Biotech.* 16:535 (1998)).

Expression of recombinant MAbs using different expression systems such as bacteria, yeast, baculovirus and mammalian cells have been reported (*Gen. Eng. News* p. 12, August (1996)). Bacterial cells produce MAbs which accumulate as improperly folded, non-native proteins in inclusion bodies. However, the levels of properly folded MAbs from industrial cell cultures are generally very low.

Humanized bispecific antibody produced from *E. coli* in secreted form was found to simultaneously bind different antigens on two different cells (Russoniello et al., *Clin. Cancer Res.* 4:2237 (1998)). Using *Pichia pastoris*, Ridder et al. have reported production of a soluble and functional rabbit single chain antibody fragment ("ScFv") (*Biotechnology* 13:255–60, (1995)). The yields of ScFv for human leukemia inhibition factor was 100 mg/L. Glockhushuber et al. reported production of single chain and Fab fragments of antibodies in *E. coli.* (*Biochem.* 291362 (1990)). The yield in this system was poor (10–100 ug/ml) with the bacterial products being secreted in the periplasm and not glycosylated, requiring solubilization, denaturation, reduction, and renaturation to facilitate the formation of intramolecular disulfide bonds and the native conformation. Glockhushuber et al., *Biochem.* 29:1362 (1990). Another disadvantage of *E. coli* derived polypeptides is endotoxin contamination which can cause immune reactions in patients. In addition, *E. coli* do not have the ability to remove the N-formyl-methionine by post-translational modification which is required for the production of functional antibody formation. Glockhushuber et al., *Biochem.* 291362 (1990).

U.S. Pat. No. 4,816,397 ("the '397 patent") describes the process for production of multichain polypeptides or proteins in a single host cell, which comprises transforming the host cell with DNA coding for each of the polypeptide chains. The invention also describes the production of recombinant IgG heavy and light chain or fragments thereof having an intact variable domain. While the '397 patent describes the production of both a heavy and light chain in a single cell, the expressed polypeptides were found in inclusion bodies in the bacterial cells in which they were produced and required cumbersome denaturation. Only a small fraction of the amount expressed was retrievable in functional, soluble form.

Feasibility of expression of functional immunoglobulin (IgG) in yeast was first reported by Wood et al. (*Nature* 314:446 (1985)) and Carlson (*Mol. Cell Biol,* 8:2638; 46, (1988)). Functional IgG against alcohol dehydrogenase was described using a yeast inducible promoter. Using GAL1-10 bidirectional promoter, Bowdish et al. (*J. Biol Chem.,* 266:11901–8 (1991)) produced properly folded Fab fragment of a catalytic antibody, permitting the expression of low levels of two antibody polypeptides simultaneously. However, the expression of heavy chain gene was more efficient than that of light chain gene from GAL1 10. The results of Bowdish et al. indicate that recombinant heavy chain polypeptides are reasonably stable in yeast cytoplasm. Typically 100–200 ug/L of Fab was expressed which accounted for approximately 0.1% of total cellular protein. In comparison to the prior art methods, an advantage of the yeast expression system of the present invention is that it can simultaneously express two proteins (or protein subunits) in similar amounts, thereby favoring higher yields of functional multichain molecules.

In addition, recombinant MAbs have been expressed in hybridoma or myeloma cell lines. See David Robinson, *Biotech Bioeng.* 55:783 (1997). The current methodologies are limited by a low secretion rate of cell lines and the difficulties of selecting human clones secreting IgG. See Bobbington et al., *Biotech* 10:169 (1992). The media contain as much as 50 ingredients, and can take up to 14 days for fermentation making development of a mammalian cells secreting MAbs slow.

In some cases the polypeptides produced by the aformentioned techniques are not immunologically functional as they are incapable of combining with complementary heavy or light chains to provide functional IgG molecules.

2.2. The Role of MAbs in Therapeutics and Diagnostics

Herceptin (Genentech, San Francisco, Calif.) was the first humanized MAb approved by the FDA for use in the treatment of human cancer. Werner, *Semin. Oncol.* 26:43 (1999). However, current MAb technology has a number of short comings. First, production is limited by low yields, long production times and high costs of production, as discussed above. Second, in non-chimeric form, MAbs are immunogenic. A major drawback of MAbs produced in ascites of mice is that these MAbs, when administered to human patients, cause an immune response which produces neutralizing human-anti-mouse antibodies ("HAMAs"). HAMAs limit the number of times a patient may be treated with a mouse MAb. Several antibody variants in which immunogenic regions have been eliminated, including chimeric and humanized antibodies, are currently being tested in therapeutic clinical settings.

It is believed that if the affinity and/or specificity of an antibody (Ab) can be improved ten or twenty fold, its therapeutic usefulness can be greatly improved. Such high affinity Abs could target specific cells. The selective delivery of drugs to a tumor is a major goal in cancer chemotherapy. Solid tumors are poorly vascularized which hinders antibody penetration. Smaller molecules such as single chain antibodies or Ab fragments may more efficiently penetrate solid tumors. The smaller molecules have reduced serum half life, enhanced tissue penetration, may be useful in tumor imaging and therapy or for the treatment of acute inflammation. However, current methods are not amenable to rapid screening of MAbs or efficient, large-scale, cost effective production of MAbs.

Therefore, it would be useful to have improved methods to quickly screen for high affinity therapeutic MAbs. Therapeutic use of MAbs may require doses ranging between several hundred milligrams to a gram over the course of therapy. Typical expression levels of hybridoma cell lines is between 0.2–0.5 g/L. Robbinson et al., *Biotech. Bioeng.* 44:727 (1994). For a moderate market like lung or breast cancer to achieve 30% market penetration, a company will have to produce 60 kg purified bulk product. Using hybridoma cell lines, this will translate to 50 runs of 14 days each for a 5000-L bioreactor which would require 2 years to produce the required MAbs (Seaver, *Genet. Eng. News,* Jan. 15, (1997)). Improved methods for the quick, low cost production of MAbs would vastly improve the introduction of therapeutic MAbs into the market.

2.3. Expression of Heterologous Proteins in Yeast

Yeast has been used in large scale fermentations for centuries and the technology of large scale production of yeast is well known. Yeast has several advantages as an expression system, namely: (1) it can be grown in higher densities than bacterial and eukaryotic cells, (2) it is capable of protein glycosylation which is important in antibody production, (3) its post-translational modification machinery can remove terminal methionines, and (4) it has post-transcriptional and post-translational modification machinery similar to that found in mammalian cells, increasing the likelihood of expression of a soluble, functional eukaryotic protein.

The products produced and secreted in yeast are easily purified because of the resistance of yeast to lysis (hydrostatic pressures), low contamination in media and low protease content in the growth media. In addition, yeast does not have endotoxin problems associated with bacteria or the viral contamination problem associated with products produced by mammalian cell culture systems. Furthermore, yeast can be grown more rapidly to high density in simple, low cost media than other eukaryotic cells and its genetics are well characterized and easily manipulated for the optimization of heterologous gene expression.

2.4. Immunotoxin Expression

Molecules commonly used to construct immunotoxins have been derived from bacteria or plant toxins. Pietersz and McKenzie, *Immunol. Rev.* 129:57 (1992). First generation immunotoxins have been constructed by linking hybridoma-generated monocolonal antibodies to purified toxins by chemical conjugation. Pastan and Fitzgerald, *Science* 254:1173 (1991); Melton and Sherwood, *J. Natl Cancer Inst.* 88:153 (1996). These were found to have limited efficacy against cancer, which led to the development of recombinant immunotoxins, which are chimeric proteins comprising a fusion of a truncated toxin and the variable region sequences of a monoclonal antibody. The improved stability, tissue permeability, and decreased immunogenicity of recombinant immunotoxins adds greater potential for the therapeutic usage of these proteins. However, concurrent with the advances in immunotoxin technology, development of cost-effective production methods are essential to provide adequate availability.

Glucose oxidase ("GO", D-glucose:oxygen 1-oxidoreductase) is an enzyme present in several Aspergillus and Penicillium species that utilize glucose as a substrate to generate hydrogen peroxide and gluconolactone as byproducts of its enzymatic activity. The functional form of the GO glycoprotein is composed of a dimer (MW 150,000) containing two bound flavin adenine dinucleotide (FAD) cofactors. Pazur et al., *Arch. Biochem. Biophys.* 111:351 (1965). The gene encoding glucose oxidase from the fungi

*Aspergillus niger* has been cloned, sequenced, and expressed in a functional form in the yeast, *S. cerevisiae*. Whittington et al., *Curr. Genet.* 18:531 (1999). In addition, the *A. niger* glucose oxidase produced from yeast has been shown to be more stable at higher temperatures and at wider pH ranges than the native protein. Frederick et al., *J. Biol. Chem.* 265:3793 (1990).

Exposure to glucose oxidase can induce toxicity in mammalian cells. Salazar and Van Houten, *Mutat. Res.* 385:139 (1997). The predominant toxic effect of GO has been shown to result from the generation of hydrogen peroxide. Starke and Farber, *J. Biol. Chem.* 260:86–92 (1985). Preferential toxicity toward tumor cells from GO-generated peroxide has also been demonstrated. Mavier et al., *Hepatology* 8:1673 (1988); Ben-Yoseph and Ross, *Br. J. Cancer* 70:1131 (1994). Purified GO induced extensive cytotoxicity (less than 10% survival) in breast, prostate, and lung carcinoma cell lines at a concentration of less than 0.01 units of activity/ml of culture supernatant within three hours of exposure. In addition, exposure of carcinoma cells to glucose oxidase may enhance radiation-induced killing through the generation of free radical species (hydroperoxides) induced by its enzymatic activity. Metosh-Dickey and Winston, *Free Radic. Biol. Med.* 24:155 (1998); Nutter et al., *J. Biol. Chem.* 267:2472 (1992); Sinha et al., *Cancer Res.* 49:3844 (1989). Glucose oxidase also can function to generate free radical products through the one-electron reduction of several different classes of xenobiotic compounds. Metosh-Dickey and Winston, *Free Radic. Biol. Med.* 24:155 (1998). Many chemotherapeutic agents (e.g. menadione, mitomycin C, adriamycin) are converted to active forms via single electron bioreduction. Nutter et al., *J. Biol. Chem.* 267:2472 (1992); Sinha et al., *Cancer Res.* 49:3844 (1989). Therefore, systemic administration of these drugs may enhance tumoricidal activity in combination with targeted exposure of tumor tissue to a glucose oxidase immunotoxin.

In addition to direct hydrogen peroxide-related toxicity, GO may also serve to deplete glucose in targeted cells. A common trait of most carcinoma cells is an extreme reliance upon glycolytic pathways to generate phosphometabolites, e.g. energy in the form of ATP, and to control the intracellular redox environment relative to normal tissue. Warburg, *Science* 123:309 (1956). This reliance is characterized by a downregulation of genes involved in oxidative phoshorylation, concomitant with increased expression of glucose uptake and transport proteins (e.g. glut1; Kozlovsky et al., *J. Biol. Chem.* 272:33367 (1997)) and glycolytic enzymes (Meixensberger et al., *Neurooncol.* 24:153 (1995)). Exposure of cultured tumor cells to hydrogen peroxide induces an increase in glycolytic metabolism and glucose uptake (Kozlovsky et al., *J. Biol. Chem.* 272:33367 (1997)), further increasing the dependence upon available glucose for survival. As a result of this chronic dependence upon glycolysis, glucose-deprivation of carcinoma cells results in significant and preferential induction of cytotoxicity (Blackburn et al., *Free Radic. Biol Med.* 26:419 (1999)).

Other oxidases have also been shown to have cytotoxic effects in mammalian cells. For example, xanthine oxidase, like glucose oxidase, induces toxicity in mammalian cells in native and modified forms. See Stanislawski et al., *Cancer Res.* 49:5497 (1989); Sawa et al., *Cancer Res.* 60:666 (2000).

It has also been shown that peroxidases, including horseradish peroxidase, eosinophil peroxidase, myeloperoxidase, and lactoperoxidase, exhibit anticancer activity when administered alone or in combination with glucose oxidases and a source of halide ions. See Everse et al., *Br. J. Cancer* 51:743 (1985); Stanislawski et al., *Cancer Res.* 49:5497 (1989); Samoszuk et al. *Cancer Res.* 54:2650 (1994); Odajima et al., *Biol. Chem.* 377:689 (1996).

Previously, several methods have been developed to deliver glucose oxidase protein into cells via streptavidin/biotin systems (Ohno et al., *Biochem. Mol. Med.* 58:227 (1996)), and liposome vehicles (Samoszuk et al., *Cancer Res.* 56:87 (1996)), and through the use of chemical conjugation to antibodies (Stanislawski et al., *Cancer Res.* 49:5497 (1989)). In each of these systems, significant cytotoxicity could be generated in the target cells. Inefficient conjugation, expense of manufacturing individual components, altered protein structure and longer production times are all disadvantages regarding the use of these procedures.

The present invention provides an improved method for producing immunotoxins which allows for the production of large amounts of immunotoxins at a relatively low cost in a short time frame. In addition, the present invention facilitates the production of various immunotoxins both analytically and in large-scale.

There is a need for an expression system for the production of functional multi-domain proteins which can reduce production times and cost. The present invention demonstrates high level expression of properly folded functional heterologous multi-domain proteins (e.g. MAbs, single chain antibodies, chimeric antibodies, immunotoxins, etc.) in yeast which is accomplished quickly and at low cost. This invention describes the use of a yeast expression system for the expression of functional multi-domain heterologous proteins.

3. SUMMARY OF THE INVENTION

This invention demonstrates the utility of a yeast expression system for the expression of functional heterologous recombinant multi-domain proteins in yeast which is cost effective and which allows for efficient production. The yeast expression system allows for the inclusion of a plurality of (up to three) modular expression cassettes which may encode multiple polypeptide chains of a heterologous multi-domain protein on a single plasmid. Because multiple polypeptide chains may be encoded by the expression cassettes of the present invention in a single vector, the system can produce equivalent amounts of each of the multiple polypeptide chains, thereby enhancing the yield of a functional heterologous multi-domain protein. For example, functional monoclonal antibodies ("MAbs") comprising a heavy chain and a light chain of an immunoglobulin ("IgG") may be produced using the yeast expression system of the present invention. In addition, functional single chain antibodies, antibody fragments and chimeric antibodies may also be produced. This invention also relates to a system for the cost effective production of immunotoxins in yeast.

The production of MAbs may be accomplished using the present invention which comprises a yeast expression system including a single plasmid comprising expression cassettes encoding both heavy and light IgG chains. This process provides a technical and practical advantage to other methods by providing better yields of functional MAb (greater than 5 mg/L from 100 ml shake flask fermentation), quicker production times, modular expression cassettes which permit production of MAbs to any specific antigen within a few weeks with little manipulation of the vector and lower costs of production.

The yeast expression system can be used for expression of a single chain, Fab fragment or a complete antibody molecule. Cotransformation of a host yeast strain with two plasmids containing heavy ("H") and light ("L") chains can also be used for expressing antibodies such that the H and L chains are produced in equivalent amounts. The yeast expression system is well suited for commercial use by providing a low cost system in which high yield expression is achieved (greater than 5 mg/L host cell culture) and the proteins produced may be secreted in the medium for easy isolation.

In addition, the present invention is directed to the production of multi-domain recombinant proteins (e.g. immunotoxins). For example, the production of functional immunotoxins may be accomplished using the present invention which comprises a yeast expression system having one or more, or a plurality of, expression cassettes wherein each expression cassette includes a nucleic acid comprising an antibody domain (e.g. scFv, Fab', etc.) fused to a toxin (e.g. an oxidase toxin such as glucose oxidase, xanthine oxidase, amino acid oxidase and peroxidases). The present invention also offers the advantage of allowing for the incorporation and coordinated expression of an accessory molecule (e.g. chaperones which may improve protein folding) into a heterologous protein production system. Co-expression of an accessory molecule may improve the production of a functional heterologous multi-domain protein. The recombinant proteins generated by this system are optimized for efficient, high-yield expression and secretion in yeast.

4. DESCRIPTION OF THE DRAWINGS

FIG. 1. Universal cloning vector.

Figure 2:
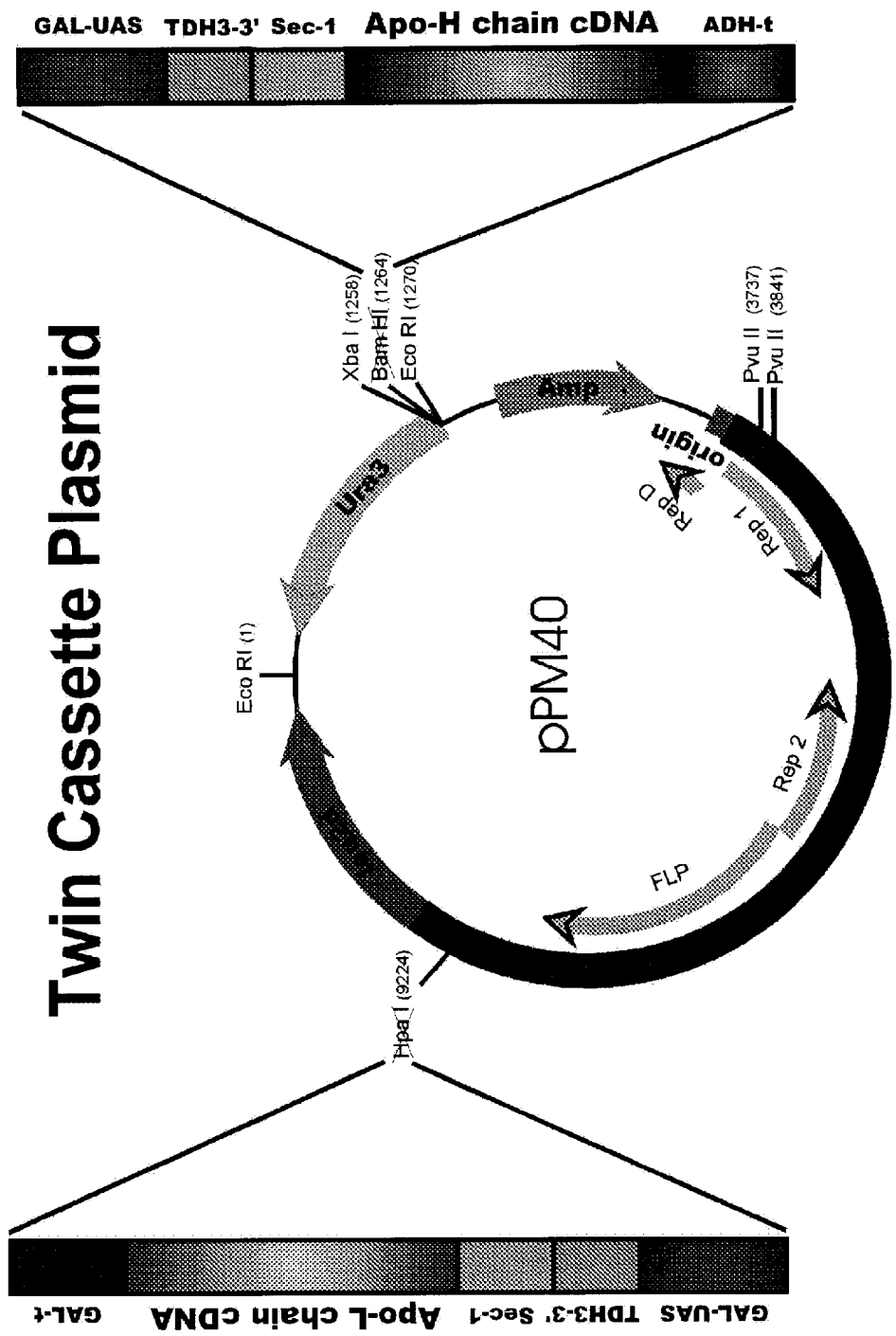

FIG. 2. A plasmid including an expression cassette comprising a nucleic acid encoding IgG light chain and expression cassette comprising a nucleic acid encoding IgG heavy chain.

Figure 3:
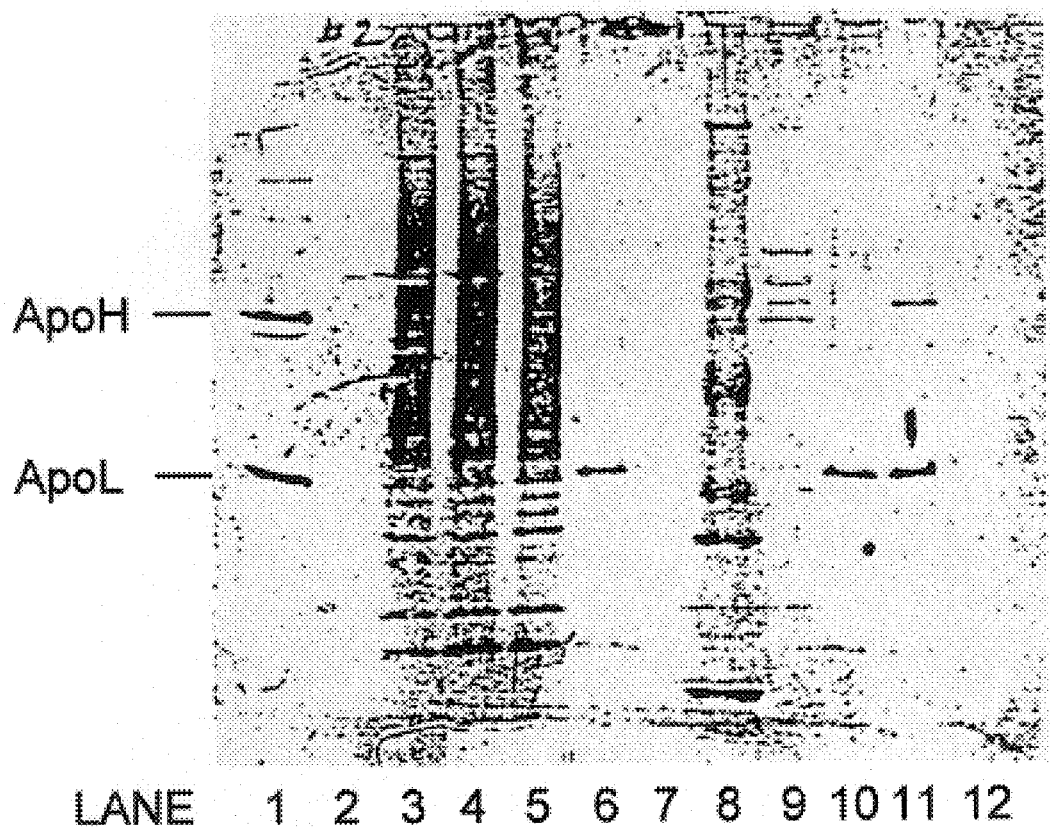

FIG. 3. SDS-PAGE gel electrophoresis of supernatants of S. cerevisiae strain Y112 transformed with the plasmid of FIG. 2.

Figure 4:
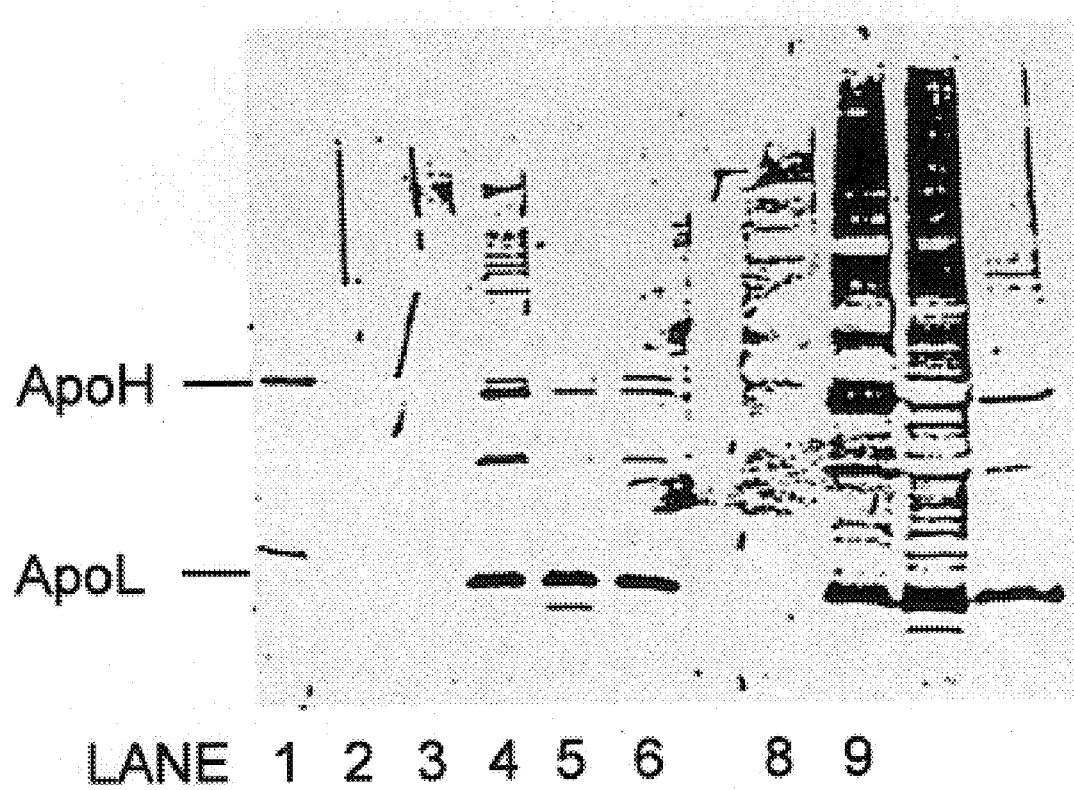

FIG. 4. SDS-PAGE gel electrophoresis of supernatants of S. cerevisiae strain Y112 co-transformed with a plasmid including an expression cassette comprising a nucleic acid encoding IgG light chain and a plasmid including an expression cassette comprising a nucleic acid encoding IgG heavy chain.

Figure 5:
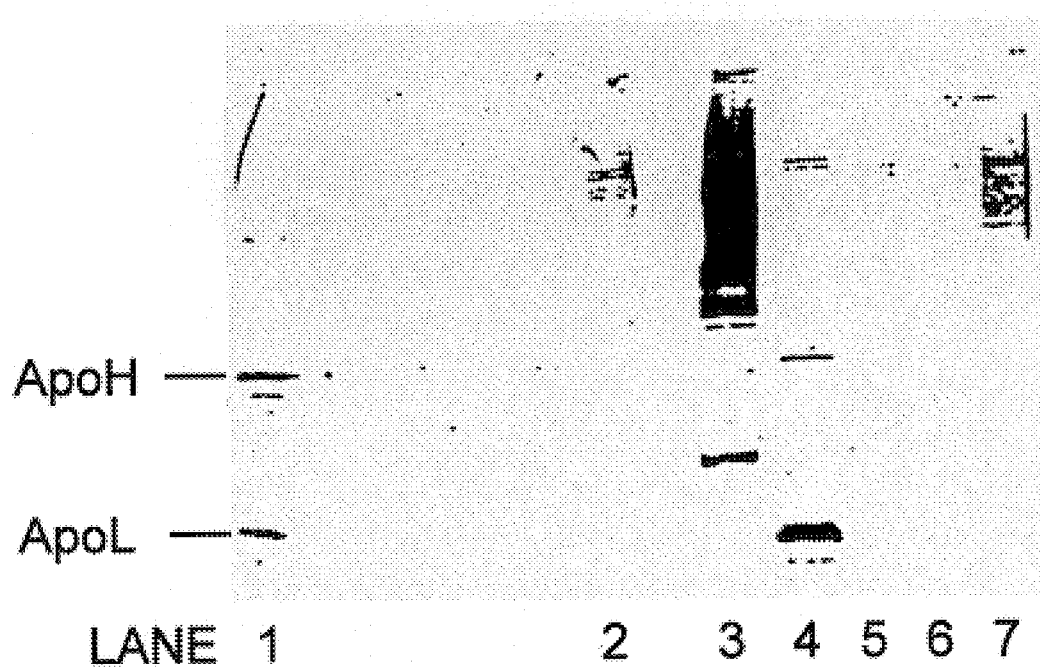

FIG. 5. SDS-PAGE gel electrophoresis of supernatants of S. cerevisiae strain Y113 co-transformed with a plasmid including an expression cassette comprising a nucleic acid encoding IgG light chain and a plasmid including an expression cassette comprising a nucleic acid encoding IgG heavy chain.

Figure 6:
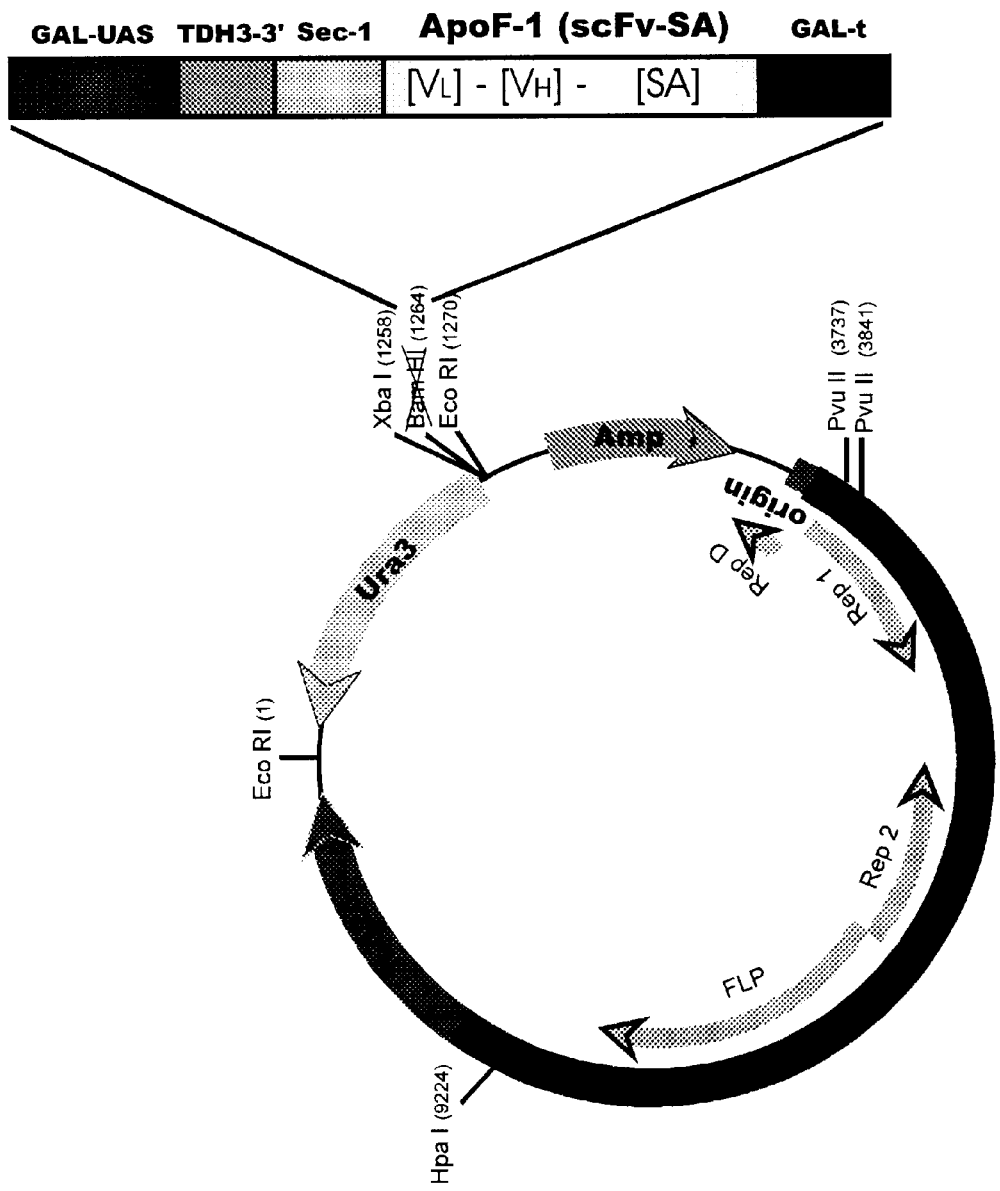

FIG. 6. A plasmid including an expression cassette comprising a nucleic acid encoding the fusion protein ScFv-SA.

Figure 7:
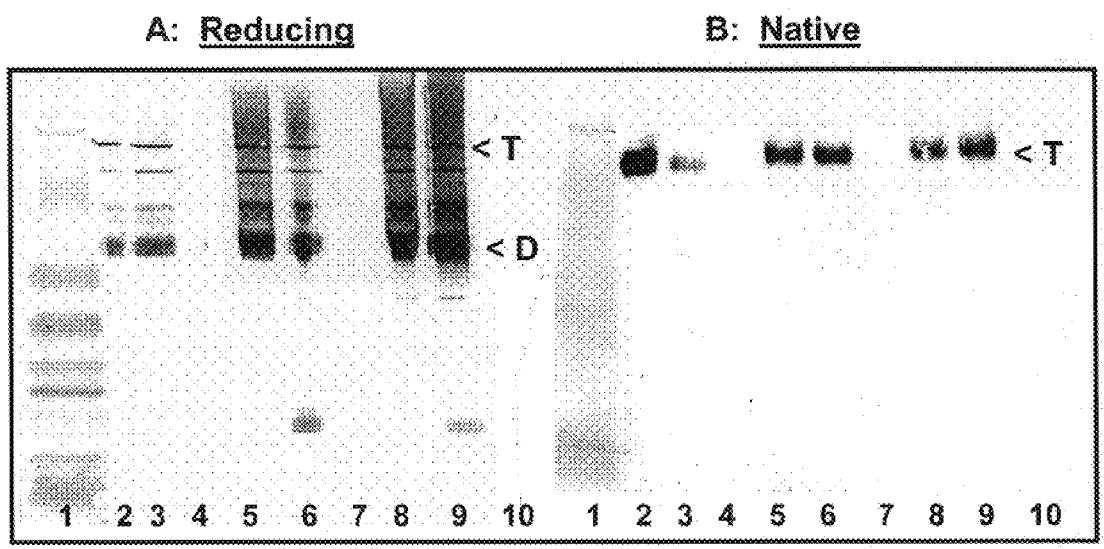

FIGS. 7A & B. Western blot analysis of both (A) SDS-PAGE gel electrophoresis and (B) native gel electrophoresis of supernatants of S. cerevisiae transformed with the plasmid of FIG. 6.

Figure 8:
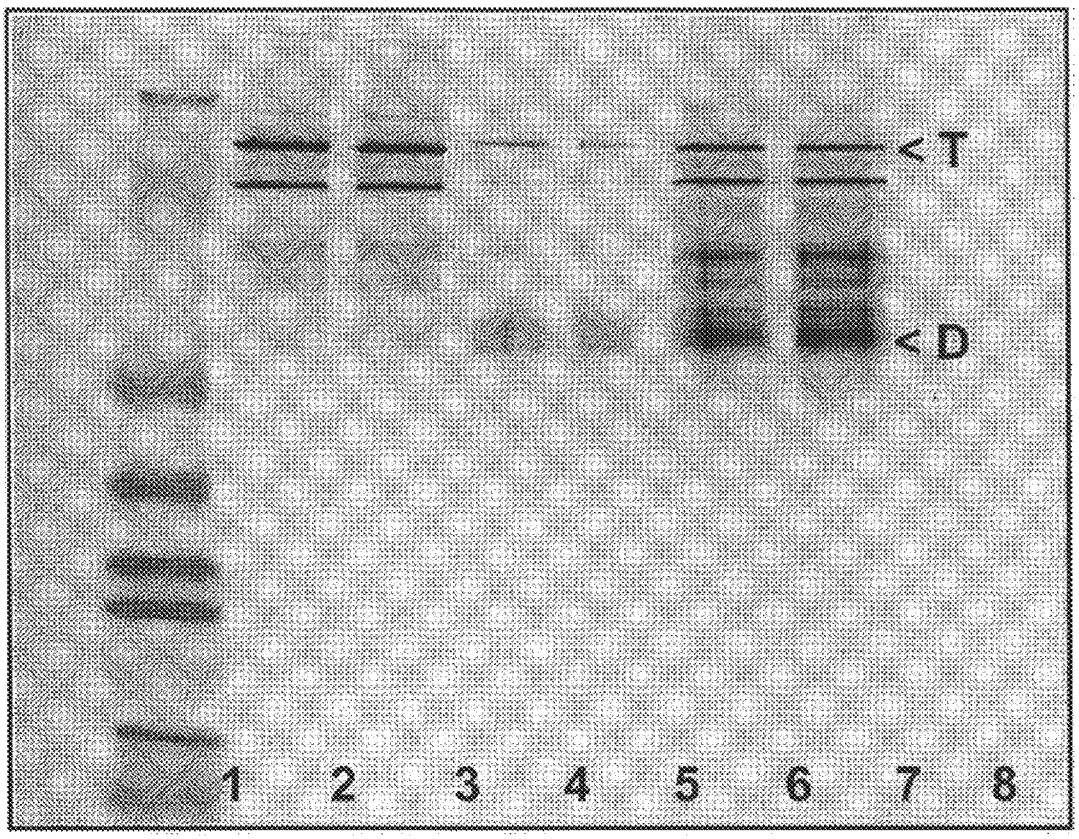

FIG. 8. Western blot analysis of SDS-PAGE gel electrophoresis of supernatants of S. cerevisiae transformed with the plasmid of FIG. 6 as compared to purified fusion protein.

Figure 9:
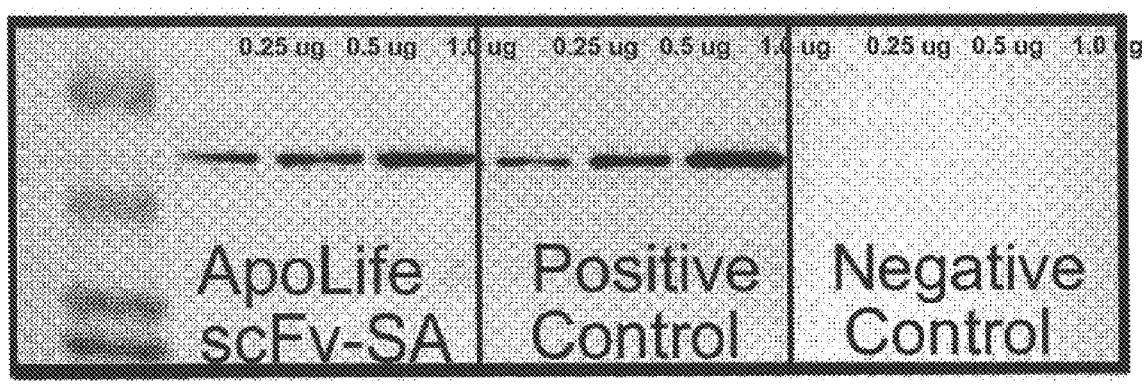

FIG. 9. Functional EGP-2 antigen binding assay for ScFv-SA of supernatants of S. cerevisiae transformed with the plasmid of FIG. 6.

Figure 10:
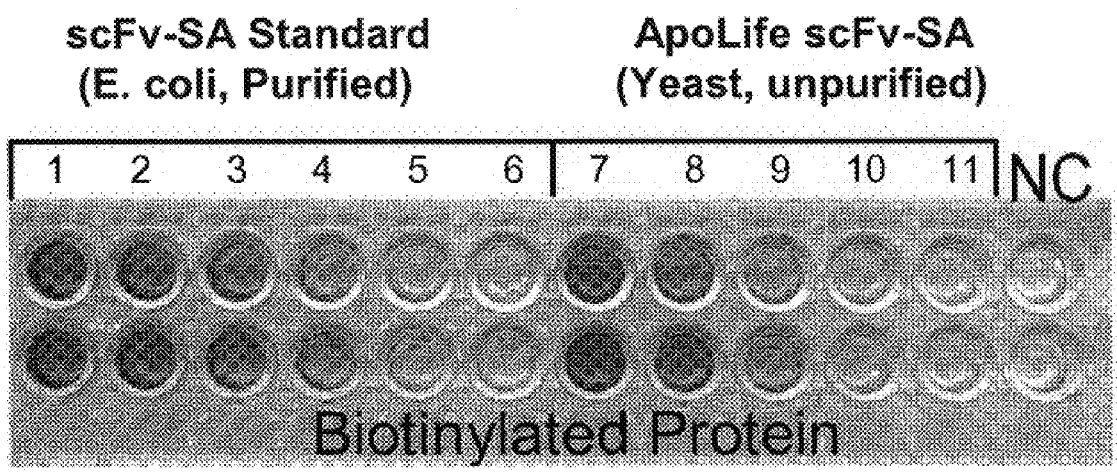

FIG. 10. Quantitation by ELISA of ScFv-SA production of supernatants of S. cerevisiae transformed with the plasmid of FIG. 6.

Figure 11:
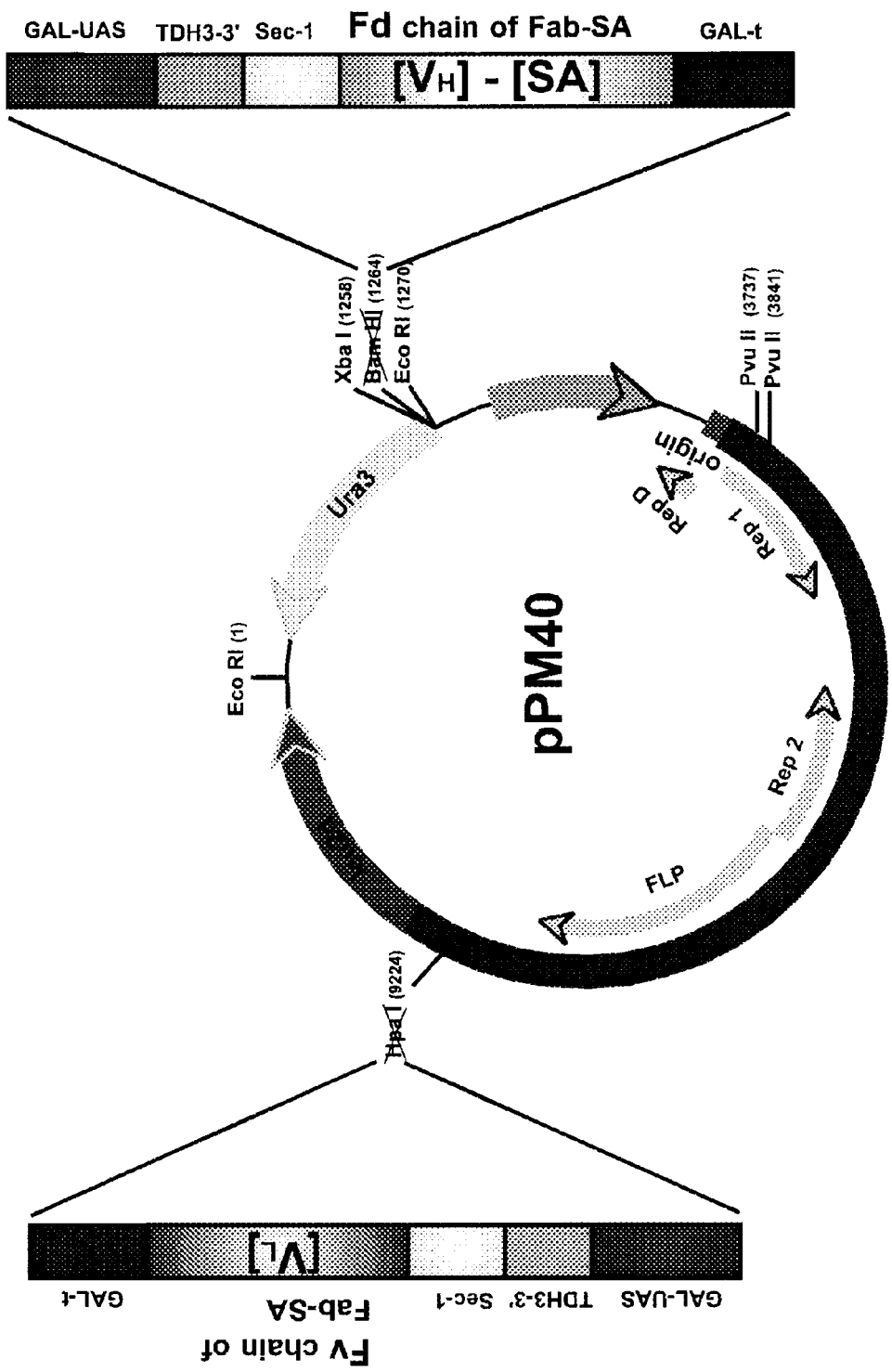

FIG. 11. A plasmid including an expression cassette comprising a nucleic acid encoding the Fd chain of Fab-SA and an expression cassette comprising a nucleic acid encoding the Fv chain of Fab-SA.

Figure 12:
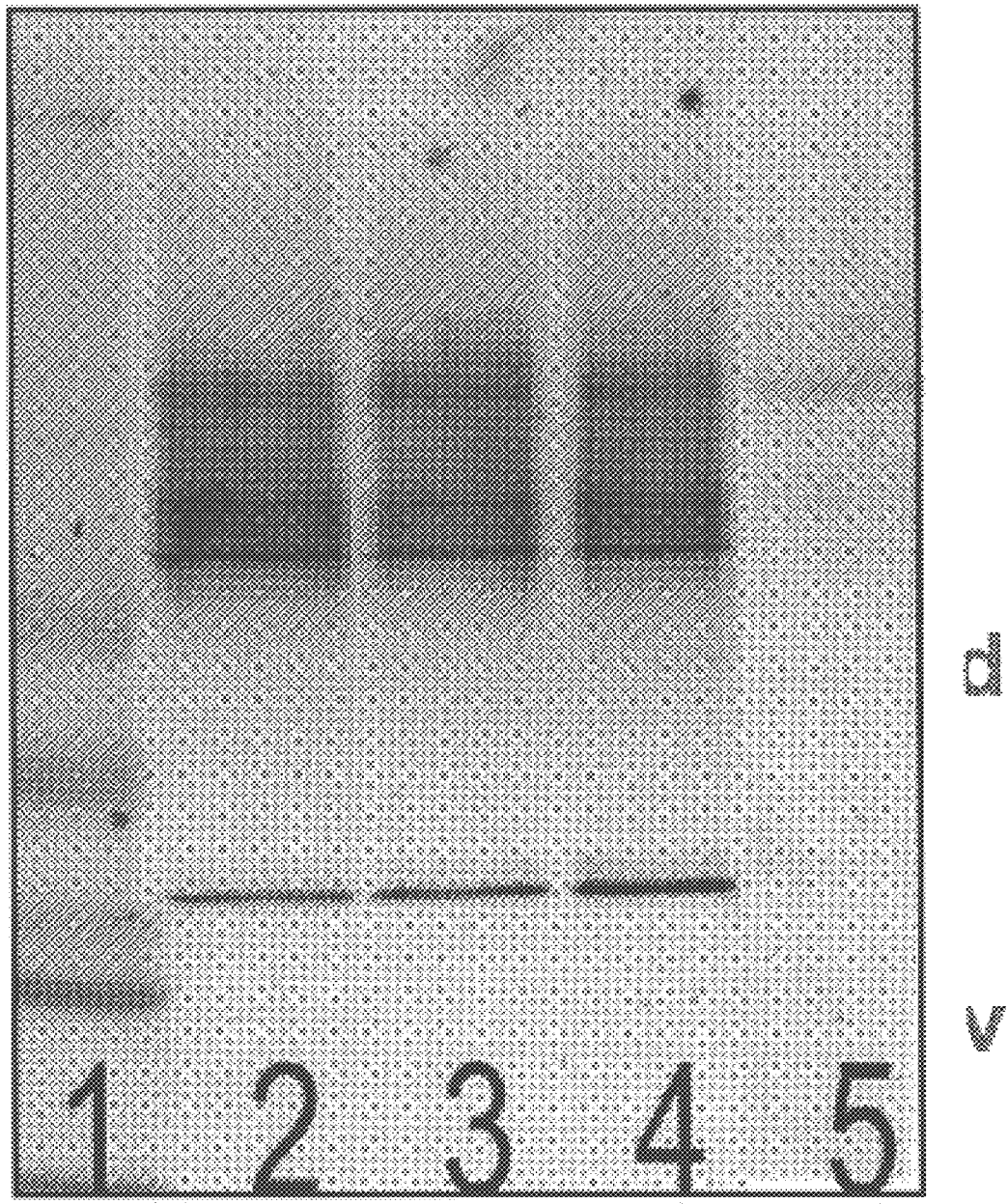

FIG. 12. Western blot analysis of SDS-PAGE gel electrophoresis of supernatants and cell lysates of S. cerevisiae transformed with the plasmid of FIG. 11.

FIGS. 13A & B. Comparison of Fab-SA expression from fermentation supernatants (panel A) and the corresponding cellular lysates (panel B) obtained from various yeast strains.

Figure 14:
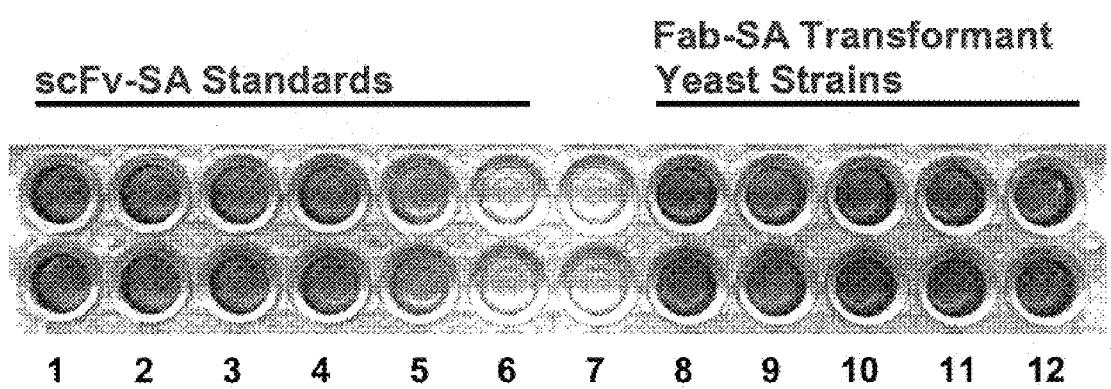

FIG. 14. Quantitation by ELISA of Fab-SA production from supernatants of S. cerevisiae transformed with the plasmid of FIG. 11.

Figure 15:
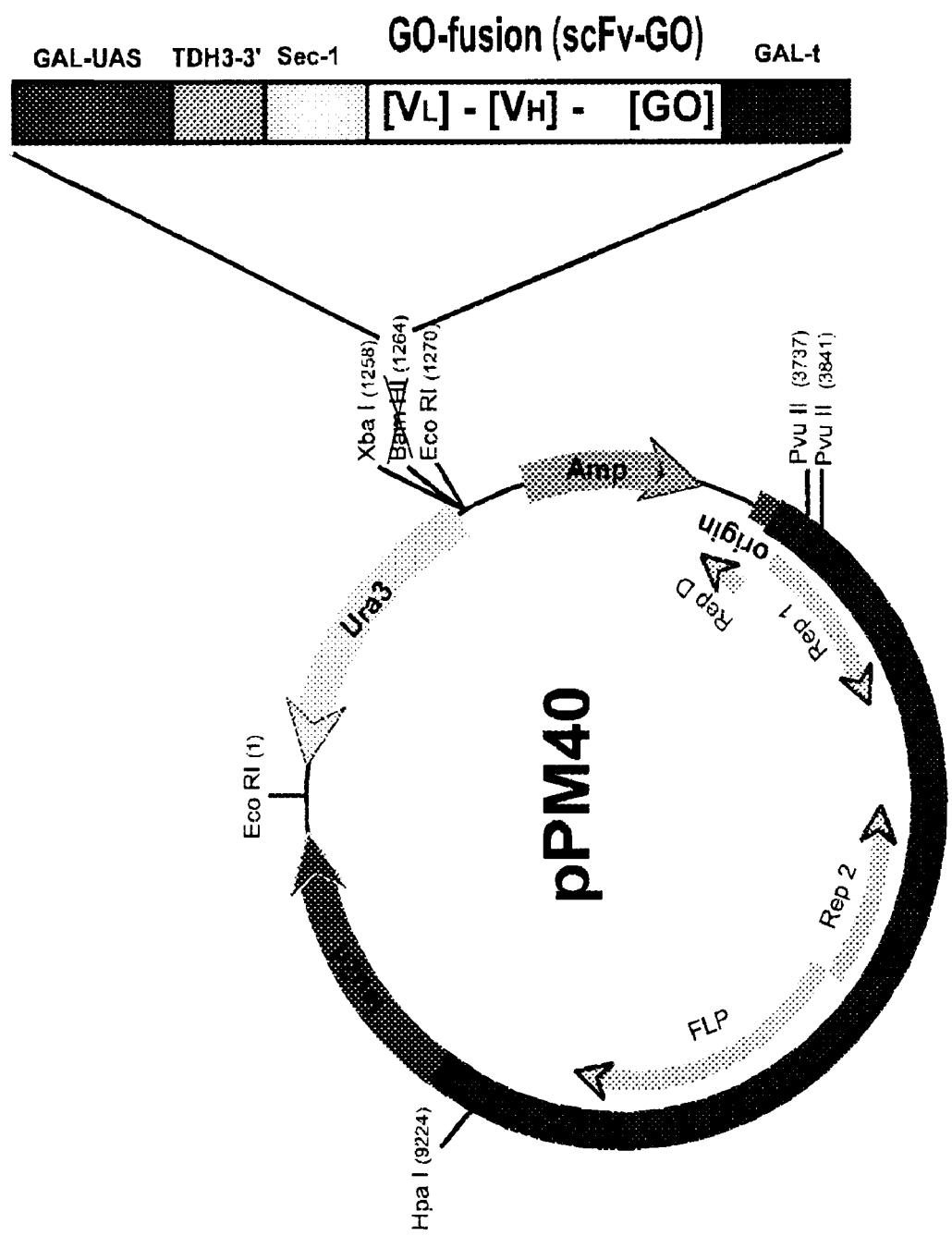

FIG. 15. Expression cassette comprising an antibody gene (ScFv) and a toxin gene (glucose oxidase).

Figure 16:
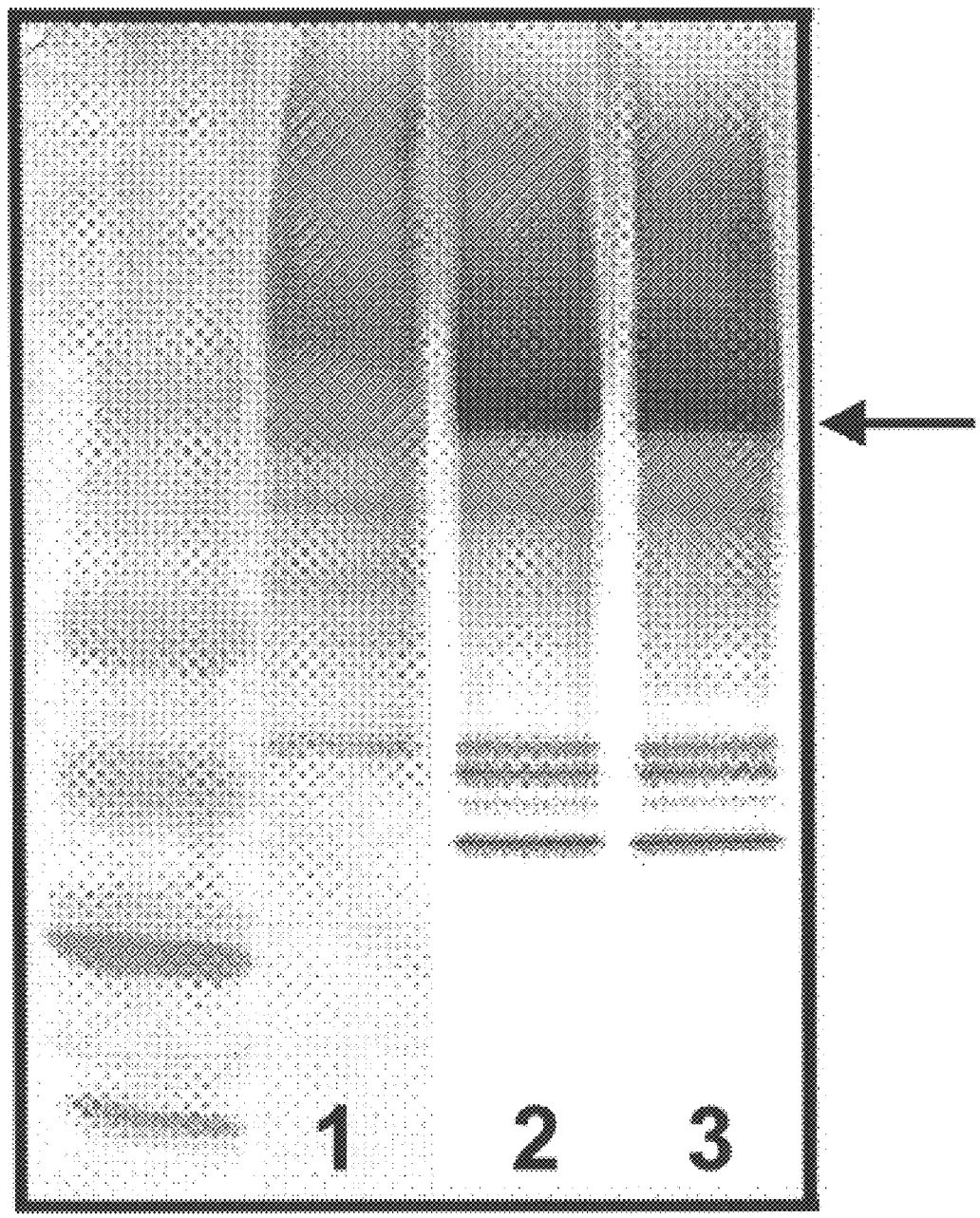

FIG. 16. Western blot analysis of SDS-PAGE gel electrophoresis of supernatants of S. cerevisiae transformed with a plasmid including the expression cassette of FIG. 15.

Figure 17:
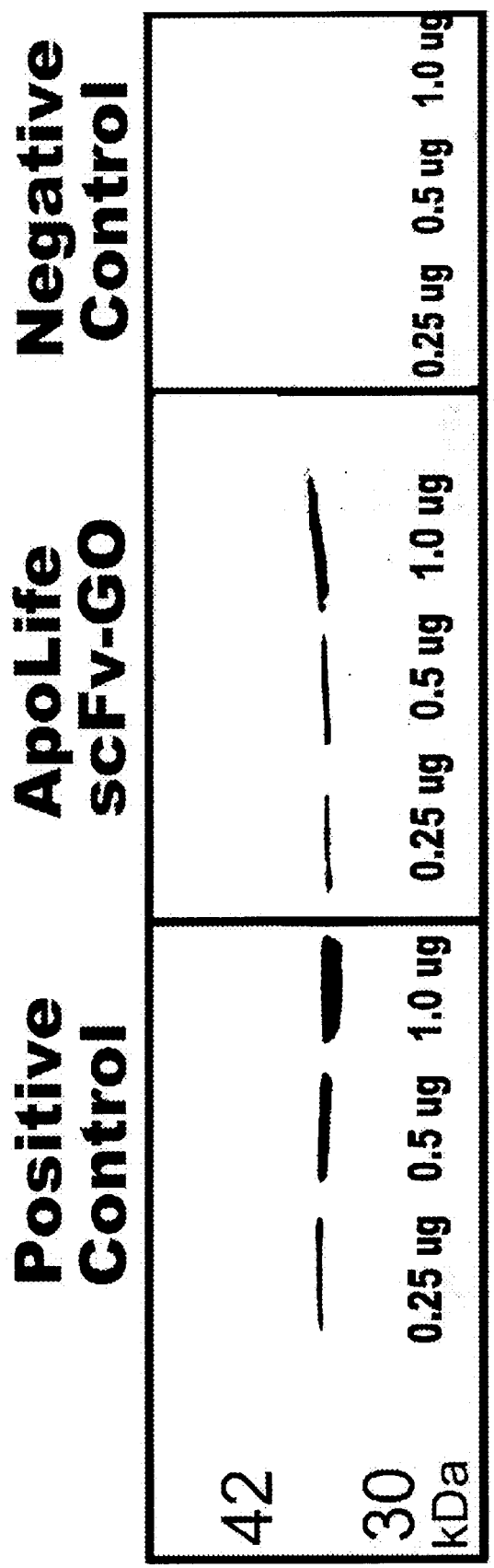

FIG. 17. Functional EGP-2 antigen binding assay for ScFv-GO of supernatants of S. cerevisiae transformed with a plasmid including the expression cassette of FIG. 15.

FIGS. 18A & B. (A) Control wells measuring the glucose activity of reagents alone, buffer (PBS), and purified glucose oxidase, (A) functional glucose oxidase activity assay for ScFv-GO of supernatants of S. cerevisiae transformed with a plasmid including the expression cassette of FIG. 15 at 0 (preculture), 24 and 48 hours post-induction, also shown is reagents alone, and vector alone control.

Figure 19:
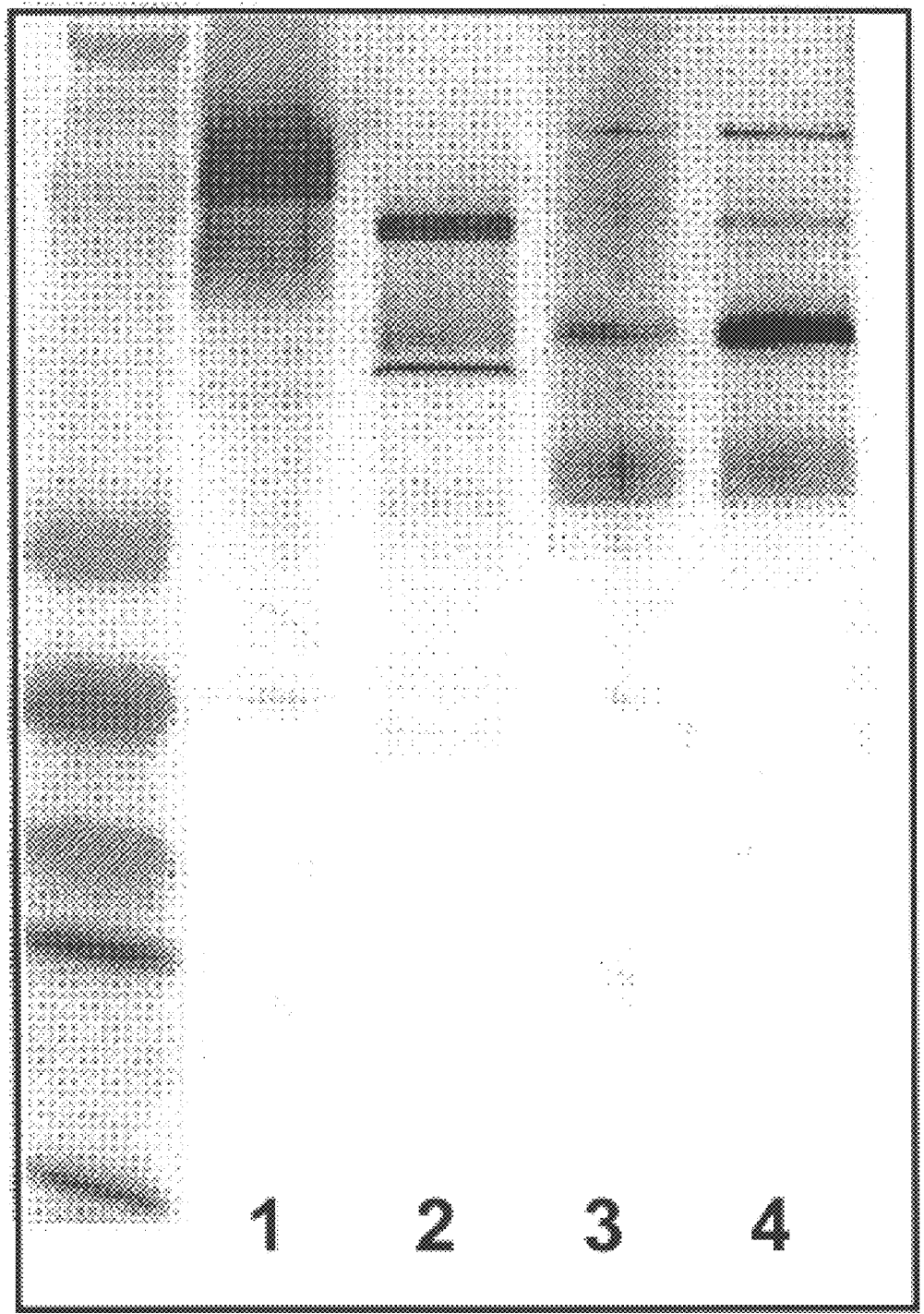

FIG. 19. Western blot analysis of SDS-PAGE gel electrophoresis showing ScFv-GO glycosylation.

Figure 20:
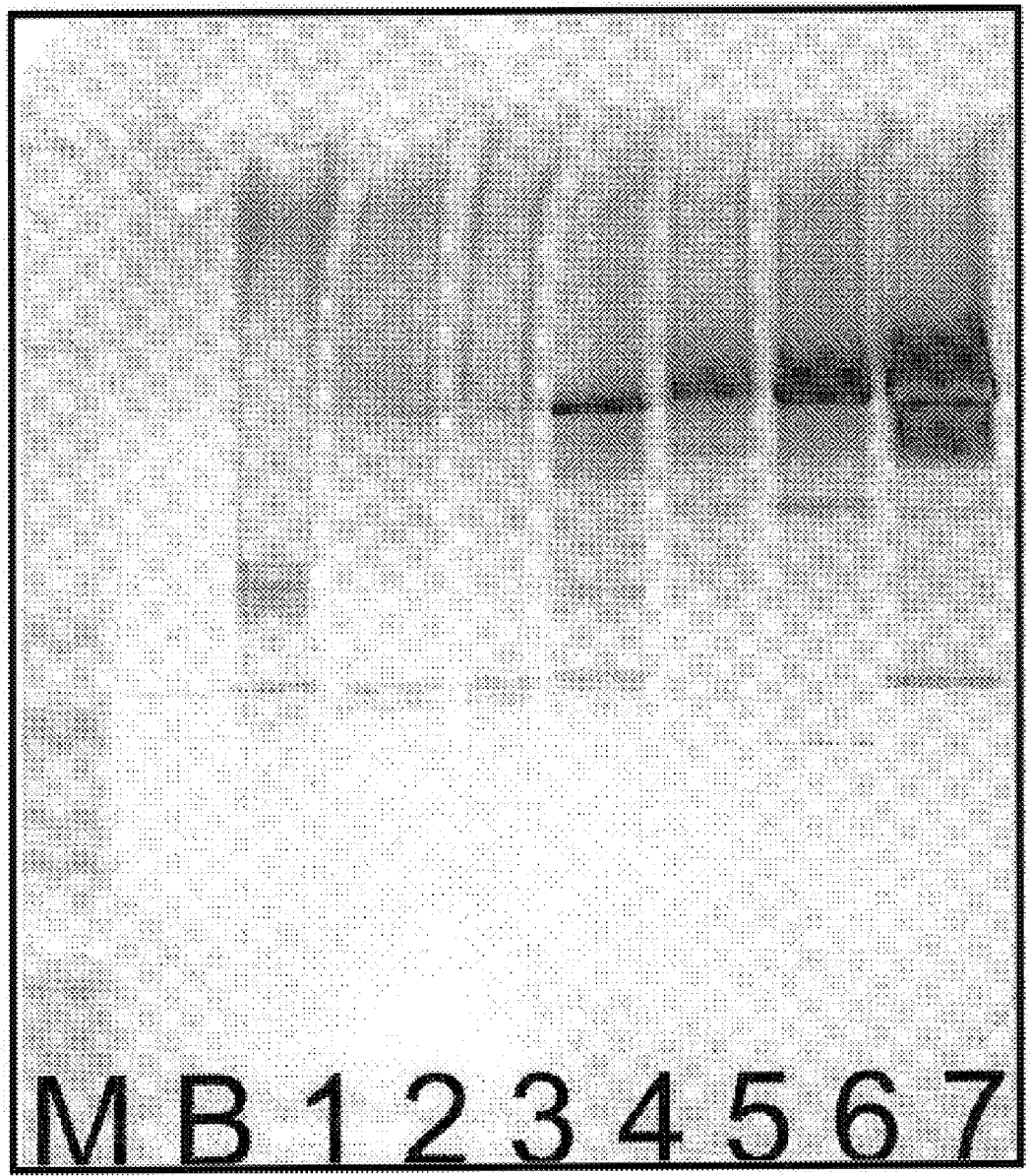

FIG. 20. Comparison of ScFv-GO expression in various yeast strains.

FIG. 21. Comparison of different media for the growth of yeast strains transformed with the plasmid of FIG. 6.

Figure 22:
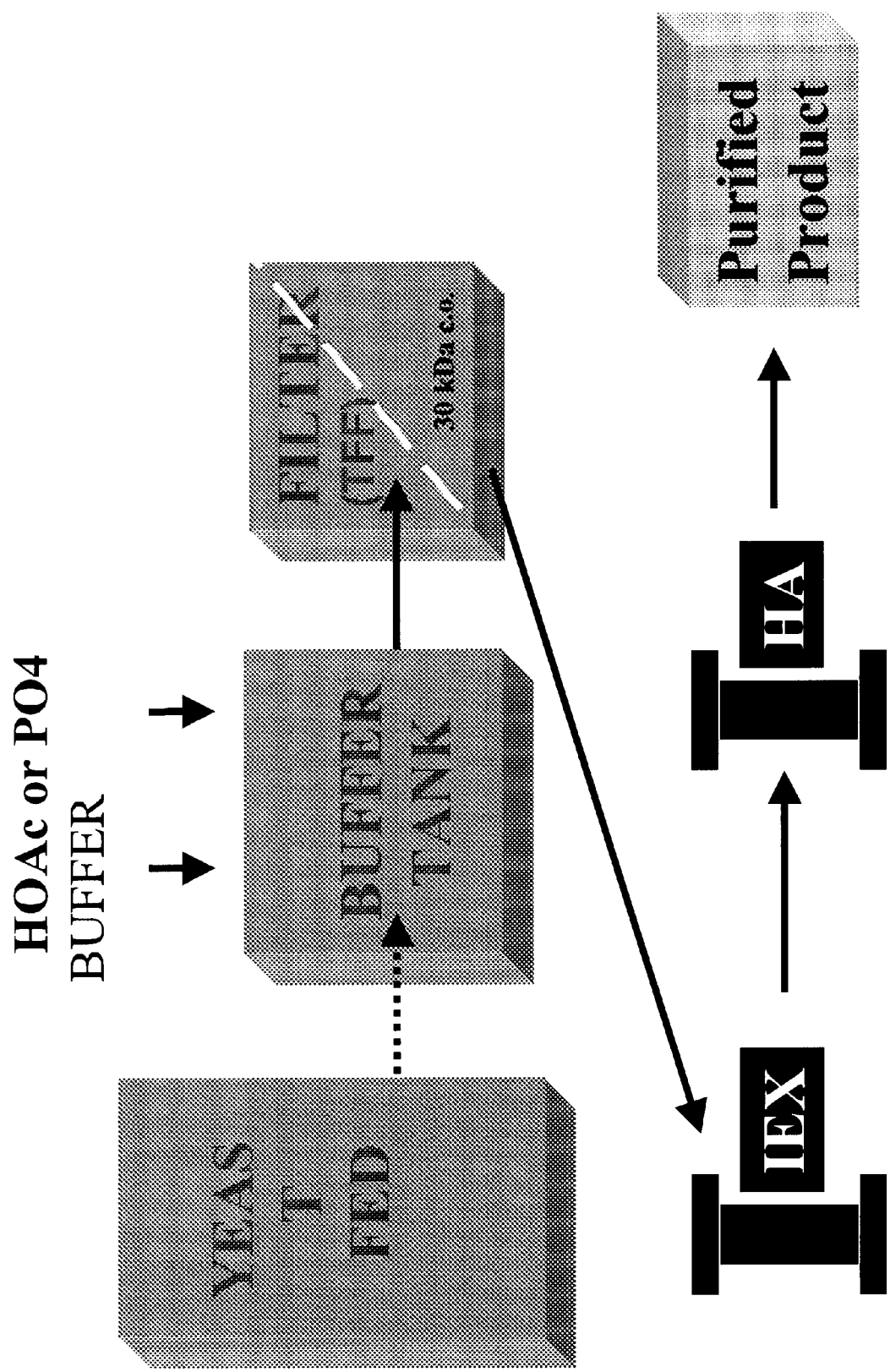

FIG. 22. Flow diagram illustrating an antibody-fusion protein purification scheme.

5. DETAILED DESCRIPTION OF THE INVENTION

For the purposes of clarity of description, and not by way of limitation, the detailed description of the invention is divided into the following subsections.

(i) the Yeast Expression System
(ii) hybrid promoters
(iii) yeast host cells
(iv) antibody expression
(v) immunotoxin expression

5.1. The Yeast Expression System

This invention describes an efficient yeast expression system for production of functional heterologous multi-domain or multi-chain proteins. The yeast expression system includes one or more, or a plurality of, expression cassettes (see, e.g., FIG. 11) comprising (a) a strong constitutive or inducible hybrid yeast promoter, (b) a leader sequence, (c) a nucleic acid encoding a heterologous protein, and (d) a transcription termination sequence. Nonlimiting examples of constitutive promoters include GAPDH (TDH3), ADH1 or the enolase promoter. As the term is used herein, a hybrid promoter comprises an upstream activation sequence(UAS) of an inducible promoter, such as GAL1, GAL10, ADH2 or PHO5 and the TATA box of a strong constitutive promoter, such as, GAPDH, GAL, ADH, enolase, etc. The expression cassette may further comprise secretion signals which may be natural signals from IgG molecules or secretory signals from non-imunoglobulin molecules (e.g. human serum albumin secretory signal, yeast secretory signal). In preferred embodiments of the invention, the yeast expression system may include a "high-copy" yeast vector comprising a plurality of expression cassettes inserted at multiple cloning sites. Where the expression cassettes encode different protein chains (e.g. heavy and light immunoglobulin chains, see FIG. 2) the high-copy yeast vector allows for the efficient expression of a functional heterologous multi-domain or multi-chain protein in yeast. A high-copy yeast vector may alternatively contain more than one expression cassette encoding the same protein.

As used herein, a functional protein refers to a protein which exhibits its wild-type function, e.g. a functional MAb binds to antigen and a functional immunotoxin binds to antigen and also retains toxin activity, although the degree of function (e.g. binding affinity or toxin activity) may be different from wild-type.

Recombinant protein production using the yeast expression system of the present invention may be confirmed by techniques known in the art, such as Western blot analysis. The system may produce recombinant MAbs and immunotoxins in excess of 5 mg/L. This yield can be improved (10×) by selection of promoters, carbon sources and fermentation conditions. Nonlimiting examples of high copy vectors include pPM40, YEp13, C1/1 and pSI. See, e.g. abstract for NSBI Grant Number 1R43AI40822-01 of Motwani (1996); available online from CRISP at the NIH wedsite, incorporated herein by reference.

The expression cassettes of the present invention allow for mixing and matching of different upstream activating sequence (UAS) elements, translation initiation sequences, promoter elements, secretory signals and nucleic acids, using cloning techniques known the art (see e.g., Fritsch and Manniatis, *Molecular Cloning: A Laboratory Manual, 2$^{nd}$ Ed.* 1989; Ausubel et al. (eds.) *Current Protocols in Molecular Biology* (1992); incorporated herein by reference). Improved yields of heterologous proteins may be achieved by such mixing and matching.

The expression system of the present invention may also include an appropriate plasmid replication signals and/or a selection marker to promote high copy number of the plasmid, and thus increase expression of the polypeptides in the yeast cells. Suitable selection markers may include, but are not limited to, leu, ura and trp etc. In a preferred embodiment of the present invention, the selection marker may be either ura or leu.

In one specific, non-limiting embodiment of the invention, the vector can include three expression cassettes which can be positioned at three restriction endonuclease sites in the high-copy vector (e.g. XbaI, Bam HI, Eco RI, sites of the pPM40 high-copy vector). The expression cassettes can be cloned in either direction (e.g. two cassettes may be cloned such that transcription proceeds in the same or opposite direction). The orientation of the cassettes may effect the yield of recombinant heterologous proteins. The location of these cassettes may also influence the expression levels of the heterologous proteins. Expression yields may be higher when a first expression cassette is cloned into the BamHI site and a second expression cassette is cloned into the PvuII site. In general, the distance between two expression cassettes in the vector is at least 2500 bases. In addition, the sequences just prior to the ATG start codon may have an affect on the expression levels of the recombinant heterologous proteins (e.g. the ATG right next to the first codon for the heterlogous protein). Yields may also be improved by including two expression cassettes comprising a nucleic acid encoding the same chain in a single plasmid such that both expression cassettes produce the immunoglobulin chain.

The yeast expression system of the present invention can produce similar amounts of a first and second protein of interest (the first and second protein may represent individual subunits of a multichain protein). As referred to herein, similar amounts means that the amount of the first protein produced relative to the amount of the second protein produced is in a ratio between 0.2:1.0 to 5:1.0 and preferably 0.5:1.0 to 2:1.0. In order to produce similar amounts of a first and second protein, a vector can be constructed which has two expression cassettes of the present invention, each of which comprises a nucleic acid encoding either the first or second protein to be expressed. A yeast cell can be transformed with the vector encoding the first and second protein, grown in culture to log phase and induced to express the first and second protein in similar amounts.

5.2 The Hybrid Promoter

The hybrid promoter of the present invention includes a first nucleic acid comprising an inducible transcriptional promoter/enhancer sequence, and a second nucleic acid comprising an RNA polymerase binding site and transcriptional initiation site. The use of regulatory sequences for controlling transcription of the structural gene of interest allows for high density growth of host cells with no or low levels of expression of the structural gene when operatively linked thereto. Gene expression may then be induced by changing the environmental conditions.

As non-limiting examples of sequences which may be used according to the invention, European Patent Application No. 132,309, published Jan. 30, 1985, discloses a plasmid containing the yeast galactose-induced promoter for galactokinase (GAL1) and UDP-galactose epimerase (GAL10), hereinafter referred to as the GAL1-10 promoter, which is bidirectional. Broach et al. (Manipulation of Gene Expression, ed. Inouye, 1983) disclose a plasmid containing a GAL10 upstream activator sequence (UAS) (herein after, GAL-UAS) which promotes transcription and an alcohol dehydrogenase transcription terminator (ADH1) sequence derived from YEp51to prevent run through transcription. U.S. Pat. No. 4,615,974 discloses the use of 5' region of the yeast phosphoglycerate kinase gene as a promoter of the transcription of interferon. When using an expression cassette comprising GAL-UAS, transformed yeast can be grown in rich media containing glycerol/lactic acid to high density and then induced by switching the carbon source to galactose.

Other genes containing elements which may be used in hybrid promoters include PHO5 and ADH2. The PHO5 gene codes for a repressible yeast acid phosphatase which is repressed at high concentrations of inorganic phosphate and is derepressed under inorganic phosphate starvation. ADH2 gene is derepressed after glucose is exhausted from the medium or when cells are shifted to a nonfermentable carbon source. ADH2 gene regulation may have advantages over other hybrid promoters because no exogenous inducer is needed for derepression which reduces the cost of induction. In addition, ADH2 derepression does not require specific host strains or mutations, so it can be used in a variety of yeast strains with varied genetic backgrounds. Optimal expression is obtained when cells reach a high density making this promoter valuable for large scale production.

In one embodiment of the present invention, hybrid promoters were constructed by fusion of the upstream activating sequence (UAS) from Gal1-10 promoter with the transcription initiation sequences of the glyceraldehyde dehydrogenase (TDH3) promoter. The expression levels of heterologous polypeptides can be increased by strong promoter sequences. When the junction between the translation initiation sequences of the nucleic acid encoding the protein of interest is flush with the promoter sequences (i.e. without extraneous sequences in between the promoter sequences and the translation initiation sequences, i.e. the ATG start codon), the expression levels may be improved. Constructs incorporating such features may be prepared using a primer-directed polymerase chain reaction by techniques known in the art. In alternative embodiments of the present invention, expression cassettes of the present invention are constructed so that the yeast TDH3 promoter sequence is linked either 3' or 5' to the coding region of the nucleic acid encoding the protein of interest.

A native yeast secretion signal sequence may be inserted into the expression cassette of the present invention at a position after the promoter sequences and preceding (in the correct coding frame) the sequences encoding the protein of interest (i.e. the secretory signal sequences are 3' to the promoter and 5' to the sequences encoding the protein of interest) such that the secretion signal sequence is operatively linked to the sequences encoding the protein of interest. Nonlimiting examples of secretion signal sequences include several yeast secretory signals (e.g. alpha mating factor), human secretory signals (e.g. human serum albumin secretory signal) and the secretory signal of the protein of interest itself.

It is possible to get a flush junction between the promoter sequences and the translation initiation sequences if a convenient restriction site is available in the 3' end of the promoter sequences and the 5' end of the nucleic acid. If the nucleic acid encoding a heterologous protein does not contain an appropriate cloning site, one can create the flush junction by making internal primers to span sequences between the 3' end of the promoter sequence and the 5' end of the nucleic acid (i.e. flush with the translation initiation sequences—the ATG start codon). By using two complementary internal primers and two outside primers, one can join any two nucleic acid molecules by polymerase chain reaction (PCR). The hybrid promoter may be constructed in such a way that one can replace the GAL-UAS with ADH2-UAS or the UAS of any other regulatory promoter sequences. The 3' end of TDH3 also can be replaced by 3' end of enolase promoter or any other strong promoter. Thus by mixing and matching different promoter elements one can easily construct several hybrid promoters which may improve expression yields of heterologous recombinant proteins.

5.3 Yeast Host Cells

A yeast host for the expression of polypeptides is advantageous for many reasons, including (1) yeast culture constitutes a well characterized secretion system, (2) there are many known leader sequences including host or heterologous signal sequences for secretion, (3) some secretory proteins have been produced in yields as great as 90% of the secreted protein, (4) only low levels of native proteins are secreted in culture medium, simplifying the purification of a target protein, and (5) correctly folded proteins are produced and intracellular disulfide bonds are formed during secretion. While a difference in glycosylation may occur in yeast as compared to other eukaryotic cells, hyperglycosylation can be reduced in vitro or in vivo by taking advantage of the extensively characterized yeast glycosylation system. For example, employing a yeast host strain containing mnn9 (Ip et al., *Biochemistry* 31:285 (1992)) may be useful to avoid hyperglycosylation. In addition, a yeast strain containing two or more genetic modifications may be used to improve the yield of recombinant proteins. In one embodiment of the present invention, the yeast host cell is *S. cerevisiae*, although other yeast may be used, such as yeast of the genus Pichia, Kluyveromyces and Hansenula. A yeast strain containing mutation(s) in its cell wall can be used to increase the secretory efficiency of the expressed recombinant protein. In preferred embodiments, the yeast host cell is *S. cerevisiae* strain Y112, Y113, Y114, Y115, Y116, Y117, Y118, Y119, Y120, Y121, Y122, Y123, Y124 or Y125.

A yeast based expression system also offers several advantages over other systems including: (1) recombinant proteins generated from yeast systems are acceptable for use as therapeutics because *S. cerevisiae* is recognized as a "generally regarded as safe" (GRAS) organism, (2) yeast is a eukaryotic organism and allows for post-transcriptional and post-translational processing and modification of proteins and is more likely to produce functional proteins than a prokaryotic system, and (3) yeast have been used in large scale fermentations for centuries, so the technology for fermenting yeast is well known and a number of yeast strains as useful hosts are commercially available. It is also known that secretory proteins can be produced from yeast. Buckholz, *Curr. Opin. Biotechnol.* 4:538 (1993). Using the yeast expression system, N-terminal processing of both alpha and beta chains of hemoglobin expressed in yeast has been observed (see, U.S. Pat. No. 5,827,693, incorporated herein by reference).

Furthermore, the cost of growing yeast is a fraction of the cost of growing other eukaryotic cell cultures. By simple manipulations of fermentation conditions, the yeast expression system can yield high levels of recombinant multi-domain proteins which can be increased by high density fermentations, complex media, proper carbon and nitrogen sources, pH, temperature, aeration (pO2), induction regimen, fed batch v.s. continuous fermentations, use of minimal salt media, and selection of yeast strains with supersecretory activity. These criteria can be manipulated for optimization of MAb yields (see, e.g., FIG. 21). Using shake flask fermentations >10 mg/L of functional recombinant multi-domain proteins may be obtainable (Motwani et al., *Proteins Expression and Purification*, 8:447, 1996). This yield can potentially be improved 2–10× when 2–10 L fermenters are used for large scale fermentations applying some of the above criteria (Motwani, et al., *Proteins Expression and Purification*, 8:447, 1996). Parameters that can be altered to increase yield include (1) carbon sources (glucose, glu+gal, raffinose, glycerol/ethanol), (2) buffering systems (e.g. phosphate, citrate), (3) media formulations (complex versus defined media), (4) vitamins (e.g. biotin), (5) trace salts, (6) induction times, (7) temperature, and (8) yeast strains (e.g. supersecretory strains, secretory mutant strains, glycosylation pathway mutant strains, permeable cell wall mutant strains, etc.).

5.4 Antibody Expression

Using an analogous yeast expression system, high level expression of functional hemoglobin has been achieved (U.S. Pat. No. 5,827,693 incorporated herein by reference). Both the alpha and beta chains of hemoglobin were expressed at equal amounts, and the recombinant hemoglobin ("Hb") was functional and properly folded. In addition, the amino terminal end of the Hb was properly post-translationally modified. Furthermore, a high yield of hemoglobin was obtained without manipulation of fermentation conditions. When two separate plasmids, each carrying an expression cassette comprising a nucleic acid encoding alpha and beta globin, were transformed in yeast, the levels of Hb production was lower than when the twin cassette plasmid including both chains was used.

Similarly, one may produce MAbs using a yeast expression system. The vector of the present invention allows for modular construction of the expression cassettes (i.e. the expression cassettes are easily exchangeable in the vector). The expression cassettes of the present invention may comprise a heavy and light chain of an IgG which may be expressed simultaneously in the yeast expression system. MAb expression yields may be greater than 5 mg/L host cell culture and preferably greater than 20 mg/L host cell culture. In a particularly preferred embodiment of the invention, the MAb expression yield is greater than 100 mg/L host cell culture. Due to the modular construction of the expression cassettes (see, e.g., FIG. 11 and FIG. 15), one can (for example by using PCR or restriction digestion) create MAbs comprising heterologous heavy and light chains or humanized or single chain antibodies with very little manipulation of the vector.

In one embodiment, a vector of the present invention allows for the expression of a functional heterologous recombinant MAb in a yeast host cell in excess of 5 mg/L of yeast cell culture. The vector may include (a) a first expression cassette comprising a nucleic acid encoding an immunoglobulin heavy chain and (b) a second expression cassette comprising a nucleic acid encoding an immunoglobulin light chain. The immunoglobulin heavy and light chain may be derived, as a specific example, and not by way of limitation, from an anti-EGP2 antibody. The functional heterologous recombinant MAb exhibits antigen binding activity similar to a MAb produced by other conventional methods, e.g. a MAb produced by an ascites fluid or a hybridoma cell line.

The functional heterologous recombinant MAb may be produced by transforming a yeast cell (e.g. S. cerevisiae) with the vector including expression cassettes comprising nucleic acids encoding an immunoglobulin heavy and light chain; growing the transformed yeast cell to log phase; inducing the expression of the MAb in the yeast cell as described in section 5.2 above; and isolating/purifying the MAb from the yeast cell culture by standard techniques (e.g. purification may be accomplished using a protein A-sepharose column).

Purification of the recombinant proteins of the present invention may be achieved by the following scheme: (1) harvesting transformed cells from large scale fermentation and separating the cells from the supernatant (e.g. by centrifugation), (2) concentrating the supernatant from the large scale fermentation up to 10 fold using a suitable molecular weight cut-off membrane filter (e.g. 30 kDa filter) by standard techniques (e.g. ultrafiltration), (3) subjecting the concentrated supernatant to conventional column chromatography (e.g. cation exchange, anion exchange, affinity chromatography, etc.), (4) purifying further by conventional column chromatography where necessary (e.g. hydroxyapatite (HA), DEAE, gel filtration, etc.).

FIG. 22 shows a general purification scheme for recombinant proteins, and particularly MAbs, produced by the present invention. The yeast are grown in a fermenter using fed batch protocols (Hensing et al., *Antoine Van Leeuwenhoek* 67:261 (1995)). The supernatant from this fermentation is then subjected to buffer exchange as shown. The sample is then circulated over a tangential flow filter (TFF) with a 30 kDa cut-off to remove lower molecular weight impurities. The sample is then purified by column chromatography using ion exchange resins (IEX, anion and cation exchange) followed by hydroxyapatite (HA) binding and elution for final purification.

The modular expression cassettes are easily interchanged allowing for mixing and matching of different proteins including mixing of domains from different species. Using this system one can readily express MAbs to any specific antigens within a few weeks (as compared to months by conventional methods) and with little manipulation of the vector. This system can be used for the production of MAbs of commercial importance (e.g. MAbs against viruses and other agents of infectious disease, receptor molecules, tumor associated antigens or cytochrome p450 isozymes).

The nucleic acids encoding IgG heavy and light chains, single chain antibodies and chimeric antibodies can be derived from naturally occurring or hybridoma (monoclonal) IgG-producing cells with the desired specificity or selected using a phage display library. The nucleic acids can also be obtained from a genomic RNA or mRNA preparation using reverse transcriptase or any other techniques known in the art.

In order to make antibodies for screening within a short time, one can clone into the vector two expression cassettes comprising either a heavy chain or a light chain by blunt end ligation using techniques known in the art to obtain several antibodies within few days. Such antibodies will not necessarily be expressed to high levels. However, once a desired antibody is isolated, yields may be improved by the techniques mentioned above in sections 5.1 and 5.3. Nucleic acids encoding different heavy and light chains may be easily interchanged by simple restriction enzyme digestions and ligations. Prototype MAbs to several antigens may be produced within a short time for testing.

It is also contemplated that a chimeric IgG molecule can be produced using this technology. These molecules can be used for immunoconjugation, immunopurification, immunoassays, cytochemical labelling, in therapeutics as conjugated to anticancer drugs or in diagnosis. The chimeric IgG molecules may be therapeutic themselves. As used herein, a chimeric IgG molecule refers to any IgG molecule comprising a variable region from one known antibody and a constant region from another known antibody which may or may not originate from the same species (e.g. a mouse variable region and a human constant region). A chimeric protein, as used herein, generally refers to a molecule comprising multiple protein domains originating from differing naturally occurring proteins, including chimeric antibodies and immunotoxins (e.g. a fusion protein of an antibody chain and a toxin, e.g., ScFv-SA and ScFv-GO of Example 5 and 6 below respectively, or a fusion protein of ScFv-SA and horseradish peroxidase).

5.5. Immunotoxin Expression

Production and therapeutic usage of glucose oxidase (GO) in the form of a single-chain, recombinant immunotoxin has not been demonstrated to date. GO conjugates have been described which are produced by isolating and purifying GO and another molecule (e.g. a peptide or monoclonal antibody) and subsequently conjugating them together using coupling techniques (see, e.g., Casentini-Borocz and Bringman, *Antimicrobial Agents and Chemotherapy* 34:875–880 (1990); Chouchane et al., *Immunology Letters* 25:359–366 (1990)). While GO is toxic to mammalian cells, it has been demonstrated that functional GO can be efficiently expressed in the yeast *S. cerevisiae* (Whittington et al., *Curr. Genet.* 18:531 (1990); Frederick et al., *J. Biol. Chem.* 265:3793 (1990)) with a very high cytotoxic potential per unit of activity. This enzyme is an excellent candidate for use in the development of immunotoxins. Recombinant immunotoxin bearing the enzymatic activity of GO may induce specific and direct cytotoxicity toward carcinoma cells that express the target antigen (e.g. EGP-2), and may sensitize carcinoma cells to chemotherapeutic agents and to radiation. The activity of GO may also inhibit tumor growth by depleting the localized levels of glucose available for glycolytic metabolism through bystander glucose deprivation and peroxide toxicity in adjacent cells.

In addition to GO, other nonlimiting examples of suitable oxidase toxins include amino acid oxidase and xanthine oxidase. Xanthine oxidase may be particularly useful when incorporated into the immunotoxins of the present invention since its enzymatic activity produces both hydrogen peroxide and the highly toxic anion radical, superoxide which may make a xanthine oxide immunotoxin very efficient. In fact, xanthine oxidase conjugated to polyethylene glycol has been shown to significantly reduce tumor growth in mice following administration of the enzyme substrate, hypoxanthine (Sawa et al., *Cancer Res.* 60:666 (2000). Therefore, immunotoxins of the present invention comprising amino acid oxidase or xanthine oxidase and antibody domains (e.g. ScFv, Fab', etc) which may specifically bind to tumor cells (e.g. carcinoma cells) are useful to induce tumor cell destruction and cytotoxicity of surrounding tumor cells.

Peroxidases are also useful in the development of immunotoxins. Peroxidases have been shown to have cytotoxic activity when administered to tumor cells, either alone or together with GO, Nonlimiting examples of peroxidases include horseradish peroxidase, eosinophil peroxidase, myeloperoxidase and lactoperoxidase.

A single-chain MAb (ScFv) directed against the human tumor-associated antigen, epithelial glycoprotein (EGP-2) has been produced (Brietz et al., *Nucl. Med.* 33:1099 (1992); Weiden et al., *J. Nucl. Med.* 34:2111 (1993)). EGP-2 expression is associated with small-cell lung cancer, lung adenocarcinomas, renal carcinomas, colon carcinomas, and breast carcinomas. De Leij et al., *Int. J. Cancer Supl.* 8:60 (1994). Therefore, ScFv may be used to target these cancer cells.

A nucleic acid encoding ScFv may be fused to the coding region of a toxin gene (e.g. an oxidase or peroxidase) from *Aspergillus niger*. In a preferred embodiment, a nucleic acid encoding ScFv may be fused to the coding region of GO. The nucleic acid encoding the fusion ScFv-GO may be cloned into an expression cassette of the present invention (see, e.g., FIG. 15) and into the vector of the present invention. A plurality of expression cassettes comprising the nucleic acid encoding the fusion protein may be cloned into the vector to improve protein yields. The modular construction of the expression cassette can facilitate the efficient construction of immunotoxins containing ScFv domains specific for other cancer antigens and/or alternative toxin (e.g. horseradish peroxidase (HRP)) molecules and thus generate series of new immunotoxins in less time than required by current methods.

The present invention is useful for the production of functional immunotoxins. As referred to herein, an immunotoxin is a multi-domain, chimeric protein containing an immunological domain (e.g. an antibody, or fragment thereof) and a toxin doman. In one embodiment, ScFv-GO immunotoxin fusion protein is produced using the yeast expression system of the present invention. In another embodiment, ScFv-HRP immunotoxin fusion protein is produced using the yeast expression system of the present invention. The ScFv-oxidase and ScFv-peroxidase immunotoxins are useful as they may specifically recognize cancer cells bearing the EGP-2 antigen and demonstrate toxicity therein thus specifically eliminating these cells. The oxidase coding sequences or peroxidase coding sequences may be cloned in the 5' (N-terminal protein position) or 3' (C-terminal protein position) orientation to achieve optimal functionality of the fusion protein. In a further embodiment, an immunotoxin comprising one chain (either heavy or light) of ScFv fused to HRP and the other chain (either heavy or light) of ScFv fused to GO may be constructed. Such an immunotoxin can form a multichain protein wherein the heavy and light chain of ScFv are bound connecting the attached HRP and GO in a single multichain molecule. Such a molecule may be administered to tumor cells for the treatment of cancer. In addition, a single chain ScFv-GO immunotoxin and a single chain ScFv-HRP immunotoxin may be administered alone or in combination to tumor cells for the treatment of cancer.

Monoclonal antibody-based compounds (MAbs) represent the single largest category of compounds in clinical drug development. Large amounts of MAb based immunotoxins are required for therapeutic use for the treatment of cancer and other diseases. The novel functional immunotoxin fusion proteins of the present invention offer several distinct advantages: (1) GO has successfully been used to induce toxicity in mammalian cells in native and modified forms, but to date, a completely recombinant immunotoxin incorporating this toxic enzyme has not been generated for use in mammalian cells and (2) they are produced using modular expression cassettes of the present invention which allow for the rapid cloning and production of secreted recombinant immunotoxins incorporating various configurations of single-chain antibodies and toxin genes.

In one embodiment, the vector of the present invention allows for the expression of a functional heterologous recombinant immunotoxin in yeast in excess of 5 mg/L of yeast cell culture. The vector includes an expression cassette comprising a nucleic acid encoding a fusion protein of an immunological molecule (e.g. anti-EGP-2 antibody ScFv) and a toxin (e.g. an oxidase toxin, or a peroxidase toxin) (see FIG. 11). The vector may also include a plurality of expression cassettes, each comprising a nucleic acid encoding a fusion protein of an immunological molecule and a toxin. The vector which allows for the expression of the immunotoxin may then be transformed into yeast. The transformed yeast may be grown to log phase and the expression of the immunotoxin may be induced as described in section 5.2 above. The immunotoxin may then be isolated from the yeast cells and the media by standard techniques known in the art. The immunotoxin thus produced is functional, i.e. is able to bind antigen and retains toxin activity. In addition, a vector comprising a first and second expression cassette may be constructed wherein the first expression cassette comprises one chain of an immunological molecule (e.g. heavy chain of ScFv) and a toxin (e.g. glucose oxidase) and the second expression cassette comprises another chain of an immunological molecule (e.g. light chain of ScFv) and a different toxin (e.g. horseradish peroxidase) wherein the two chains of the immunological molecule are capable of binding to one another to form a multichain molecule comprising heavy and light chain each fused to two different toxins. Such a multichain molecule may be produced by the yeast expression system of the present invention. Two vectors may also be constructed, one vector comprising an expression cassette encoding a first immunotoxin (e.g. heavy chain ScFv/GO) and a second vector comprising an expression cassette encoding a second immunotoxin (e.g. light chain ScFv/HRP). A yeast host cell may be transduced with both vectors to produce the multichain molecule comprising heavy and light chain and two toxins.

Expression yields of the immunotoxins of the present invention may be improved using yeast strains overexpressing catalase (for the detoxification of $H_2O_2$) which may better tolerate a peroxide-producing immunotoxin of the present invention. Such strains may be readily isolated by simple selection techniques applied to yeast cells expressing the immunotoxin which grow to higher density. For example, yeast cells that grow well despite the presence of hydrogen peroxide in the growth medium may be selected by simple selection techniques. Also, alternative promoter/fermentation schemes may be used (ethanol fermentation) to bypass glucose exposure and utilization to improve upon the yield of recombinant immunotoxin fusion proteins. The ScFv-toxin fusion protein expression yields may be greater than 1 mg/L host cell culture and preferably greater than 5 mg/L host cell culture. In a particularly preferred embodiment, the ScFv-toxin fusion protein expression yields may be greater than 10 mg/L host cell culture and preferably greater than 20 mg/L host cell culture. In addition, fermentation using carbon sources other than glucose (e.g. glycerol/ethanol, raffinose, etc) to avoid generation of hydrogen peroxide during the course of fermentation may be used since glucose oxidase generates hydrogen peroxide through the enzymatic conversion of glucose.

In addition, alternative toxin and "suicide" genes (encoding enzymes which directly indue toxicity or activate toxic forms of prodrugs) may be used in place of oxidases and peroxidases. It may be advantageous to enhance the immunotoxin Fv region stability and specificity using mutagenesis to introduce disulfide-linkages between Fv domains. Reiter and Pastan, *Clin. Cancer Res.* 2:245 (1996). Optimization of immunotoxin expression may be achieved via further strain selection and manipulation of fermentation conditions. Furthermore, it has been shown that overexpression of either the molecular chaparone BiP or protein disulfide isomerase (PDI) (Shusta et al., *Nat. Biotech.* 16:773 (1998)) can increase secretion of single-chain antibodies 2–8 fold. Therefore, the immunotoxin fusion proteins may be co-expressed with immunoglobin chaperones (BiP, PDI) for the optimization of correct folding, transport and secretion of the expressed immunotoxin fusion protein.

The invention is further illustrated by reference to the following examples.

6. EXAMPLES

Example 1
Hybrid Promoter Production
A. GAL-UAS

Broach et al. (Manipulation of Gene Expression, ed. Inouye, 1983) disclose a plasmid containing a GAL10 upstream activator sequence (UAS) (herein after, GAL-UAS). GAL-UAS was synthesized by using YEp51 plasmid DNA (Bitter and Egan, *Gene* 69:193 (1988) and nucleic acid primers containing appropriate cloning sites (shown in lower case):

5' primer: TtgagctcCCCAGAAATAAGGC- (SEQ ID NO:1)

3' primer: AGAAGGTTTTTTTAGcccgggCA- (SEQ ID NO:2)

B. ADH-2-UAS

ADH2 gene is derepressed after glucose is exhausted from the medium or when cells are shifted to a nonfermentable carbon source. ADH2 gene regulation may have advantages over other hybrid promoters because no exogenous inducer is needed for derepression which reduces the cost of induction. In addition, ADH2 derepression does not require specific host strains or mutations, so it can be used in a variety of yeast strains with varied genetic backgrounds. Optimal expression is obtained when cells reach a high density making this promoter valuable for large scale production. ADH2-UAS was synthesized by PCR using YEp51 plasmid DNA and the following primers:

5' primer: 3' CGA TCG gagctc ATT AAC GCC TTT CGC TCA TAA-5' (SEQ ID NO:3)

3' primer: 3'-G TGT CCT CTC GTA TCT TTA CCC CAA aga tct GCG CGA-5' (SEQ ID NO:4)

C. 3' end of TDH3 Promoter

The TDH3-3' promoter fragment, which is a transcriptional initiation region from the yeast glyceraldehyde-3-phosphate dehydrogenase gene was synthesized by PCR using appropriate primers and template from plasmid gp491. The primers used were:

5' primer: 5' AtcccgggAAGGTTGAAACCAGTTCCCTG-3' (SEQ ID NO: 5)

3' primer: 3'-GTGTGTATTTATTTGTTTTACCacgtgcGC-3' (SEQ ID NO: 6)

D. 3' end of the Enolase Promoter

The enolase promoter RNA is most abundant RNA in vegetative yeast cells. The downstream element including the TATA box (ENO-3') of the enolase promoter was used for construction of a hybrid promoter, ADH2-UAS-ENO-3' (AE). The 3' end of the enolase promoter was synthesized by using plasmid DNA from pENO8-1 (Cohen, R., Holland, J., Yokoi, T., and Holland, M., Mol. Cell Biol. 6, 2287, (1986)).

5' primer:
5'-CCG GCC GTC tctaga TCT GGC TTT GAT CTT ACT ATC ATT TGG-3' (SEQ ID NO: 7)

3' primer:
3'-G TAT TGT GGT TCG TTG ATT ATG ATA TTG ATA GTT ATT ATT AC gtgcac G GCG-5' (SEQ ID NO: 8).

The 340 bp fragment containing 3' end of enolase promoter was synthesized by PCR.

E. Cloning the Hybrid Promoter into a Vector

All the fragments containing ADH2-UAS, GAL-1-10 UAS, TDH3-3' and Enol-3' were cloned into pUC19 vector. A hybrid promoter can be constructed by simple cloning of one of the UAS fragments with the strong promoter fragments. e.g. GD contains GAL-10-UAS (G) and TDH3-3'(D).

Example 2
Terminator Production
A. ADH-terminator

ADH1-transcription terminator (ADH-t) sequences were isolated from plasmid AAH5 (Ammerer, G., 1983, Methods in Enzymology, 101, pp. 192–201). Plasmid AAH5 was digested with BamH1 and HindIII. The resulting 450 bp fragment was isolated by gel electrophoresis and further digested with SphI. The 320 bp fragment of ADH-t (HindIII/SphI) was used for cloning into pUC19 vector and the plasmid was labeled pUC19-ADHt. The restriction sites on the terminator can be altered by PCR.

DNA ligation and transformation of *E. coli* was carried out using standard procedures (Laboratory Cloning,: Sambrrok, J., Fritsch, E. F., and Maniatis, T. eds., Cold Spring Harbor Laboratory Press, 1989, Second Edition). Transformed cells were plated on LB-media with 100 mg/L ampicillin. Plates were incubated at 37° C. overnight.

Example 3
Plasmids

Plasmid pUC19-GH contains a hybrid promoter which was constructed by the fusion of the upstream activating sequence (UAS) of GAL1-10 promoter (G) with the downstream promoter elements of the TDH3 promoter. The TDH3-3' promoter segment includes the transcriptional initiation site, the "TATA" sequences, capping sequence and RNA polymerase binding site. The hybrid promoter fragment was cloned into pUC19 as SacI/SphI fragment and the resulting plasmid was labeled pUC19-H.

Example 4

Antibody Production

A. Construction of Universal Plasmids Containing a GH Hybrid Promoter, Yeast Alpha Factor Secretory Signal and ADH or GAL-terminator These plasmids were constructed as a modular unit, and each fragment was cloned into the appropriate site into the Bluescript vector SK+ (Invitrogen, San Diego, Calif.) (FIG. 1).

Plasmid pUC19-GH (U.S. Pat. No. 5,827,693) contains a hybrid promoter which was constructed by the fusion of the upstream activating sequence (UAS) of GAL1-10 promoter (G) with the downstream promoter elements of the TDH3 promoter (referred to as TDH3-3' and labeled as H in plasmid pUC19-GH). The TDH3-3' promoter segment includes the transcriptional initiation site, the "TATA" sequences, a capping sequence and a RNA polymerase binding site (U.S. Pat. No. 5,827,693). Using the DNA from pUC19-GH as a template and primers containing required restriction sites, a GH promoter fragment was synthesized by PCR {KpnI (5'end) and SalI (3' end)}.

Genomic DNA was isolated from a strain of S. cerevisiae and a yeast signal, the -mating factor secretion signal, was synthesized by PCR using appropriate primers. The resulting fragment was labeled Sec1 and contains SalI (5' end) and EcoRI (3' end) restriction sites.

The transcription termination sequences of ADH and GAL10 were cloned into the pUC19 plasmid, which resulted in plasmids pUC-19-ADH-t and pUC-19-GAL-t. PCR was used to create appropriate cloning sites compatible with the nucleic acids encoding antibody heavy or light chains.

Bluescript SK+ vector (Stratagene, La Jolla, Calif.) was used for cloning the fragments of expression unit synthesized by PCR. The hybrid promoter GH was synthesized by PCR to contain KpnI (5' end) and Sal I (3' end) sites. A yeast secretory signal containing SalI (5' end) and EcoRI (3' end) was synthesized by PCR. The SK+ DNA was cut with KpnI and EcoRI. Three way ligation was set between the vector, GH promoter cut with KpnI/SalI, and yeast signal sequence cut with SalI/EcoRI. The E. coli transformants were identified by digestion with PvuII. This plasmid is referred to as pSK+-Sec1 and was cut with NotI/SacI. The ADH terminator synthesized by PCR was cut with NotI/SacI and ligated to the SK+GH-Sec1 cut plasmid. The positive clones were identified by digestion with PvuII. Plasmid containing the GH promoter, yeast factor signal and ADH-terminator was labeled SK+-GH-Sec1-ADH-t. Similarly, a GAL terminator synthesized by PCR was cloned as a NotI/SacI fragment into SK+-GH-Sec1 and this plasmid is SK+-GH-Sec1-GAL-t (FIG. 1).

Sequences upstream of ATG of cDNA are critical for high level expression of proteins (U.S. Pat. No. 5,827,693, incorporated herein by reference). Since there is a convenient site at the 3' end of the secretory signal, XhoI, we used this site for cloning. This strategy can only be used for the cDNAs that do not contain an internal XhoI site.

Nucleic acids encoding heavy (Apo-H) and light chain (Apo-L) of NR-LU-10, hereafter referred to as NRX1 (NeoRX, Seattle, Wash.) were cloned in universal plasmids (pBluescript SK+, Stratagene, La Jolla, Calif.).

B. Cloning of H and L into Universal Plasmids pApo-U1 and pApo-U2

Appropriate modification of NRX1 cDNAs were carried out using PCR and cloned into universal vectors, p-Apo-U1 and p-Apo-U2 (ApoLife, Inc., Detroit, Mich.). The resulting clones were identified by digestion with PvuII. Plasmids are labeled SK+GH-Sec-Apo-L-Gt and SK+-GH-Sec-Apo-H-At.

C. Yeast Shuttle Vector Containing LEU2 d Marker—Plasmid pPM40

The multi-copy E. coli/S. cerevisiae shuttle vector pPM40, used in the present invention, contains three cloning sites, BamHI, PvuII and HpaI which allows cloning of two cDNAs in a single plasmid. The vector also contains LEU2-d, which represents a truncated LEU2 promoter that is expressed at very low levels. When introduced into a leu2 auxotrophic strain, selection for leucine prototropy results in amplification of the plasmid to a high copy number (Erhart and Hollenberg, Bacteriol. 156:483 (1983)). Under appropriate fermentation conditions, one can select for transformants containing high copy plasmid (200 copies/cell) using this vector.

D. Cloning of Expression Cassettes for L and H Chains into Yeast Vector, pPM40

The cassettes GH-Sec-Apo-H-At and GH-Sec-Apo-L-Gt were excised and cloned separately into pPM40 at BamH1 by blunt end ligation (FIG. 2). The clones were identified by EcoRI digestion. The DNA from each plasmid was transformed into yeast to check for the expression levels of single chains. An expression vector was obtained by cloning both cassettes on pPM40 vector (FIG. 2). There are three cloning sites in pPM40. The expression levels may vary depending upon the site of cloning.

Transformation of yeast strains by electroporation with DNA from plasmids was carried out by a modification of a standard electroporation protocol. The cells were grown in YEPD (Sherman, Methods in Yeast Genetics (1986)) containing 2% glucose at 30° C. in a shaker for 4–6 hrs to create a stock. 100 ml of the same media was innoculated with the stock and grown to an OD600 of 1.3–1.5. Cells were harvested by centrifugation at 5,000 rpm for 5 min, washed 3× with distilled water and washed 2× with 1M sterile sorbitol at 4° C. The cells were resuspended in 100 ul of 1M sorbitol, and 40 ul of cell suspension was added to Eppendorf tubes. Approximately 1000 ng of plasmid DNA were added to the cells. The cells and plasmid DNA was incubated on ice for 5 min and transferred to 0.2 cm electroporation cuvettes. A Bio-Rad Gene Pulser (Richmond, Calif.) was used according to manufacturer's directions to perform the electroperation. The transformants were selected on YNB media (Sherman, Methods in Yeast Genetics (1986)) lacking uracil. With every experiment, a control was included of the yeast strain with no DNA. No colonies were seen on control plates.

Yeast strains were cotransformed with two plasmids, one containing NRX1 (heavy chain; ApoH) and the other containing NRX1 (light chain; ApoL) to see if simultaneous expression of both chains is possible from separate plasmids.

E. Standard Fermentation Conditions

A preculture was grown in 100 ml YNB media (ura-, leu+) +2% glucose for 24 hrs at 30° C. This was followed by inoculation in 200 ml fermentation media, (ura-, leu-) +2% glucose, at 0.5 OD. The cultures were grown and harvested and samples taken at various time points and induced with 2% galactose. The cells were separated from the culture media by centrifugation. The samples were then analyzed immediately as described below.

F. Analysis of Recombinant Proteins by Western Blot Analysis

The yeast cells and media collected at different time points during fermentation were stored at −20° C. The culture supernatants were concentrated with Centricon 30 filters by ultrafiltration and used for SDS-PAGE analysis. Cell pellets (10 OD) were disrupted by vortexing with autoclaved glass beads (40 mesh, BDH) in 50 mM Tris-HCL, pH 7.6, 1 mM EDTA. The mixture was centrifuged and the supernate was stored at 4° C. For electrophoretic separation, the samples were denatured under reducing conditions in the buffer: 1.5% w/v SDS, 2.5% v/v bromophenol blue, 5% v/v glycerol, 2.5% β-mercaptoethanol. SDS-PAGE analysis and transfer of proteins to nitrocellulose membrane was carried out using a Novex apparatus (Novex, San Diego, Calif.) using precast 14% and 4–20% gradient Tris-glycine gels according to the manufacturer's directions. Western blot analysis was carried out using peroxidase labeled goat anti human kappa light chain specific antibody and IgG gamma heavy chain specific antibody (Southern Biotechnology, Inc., Burlingame, Calif.) and detection was carried out using TMB reagent (Vector Laboratories, Burlingame, Calif.). If protease associated degradation of proteins was observed, 0.5 mM PMSF was included in buffers. Molecular weight standards were obtained from Novex (San Diego, Calif.).

G. Results of Western Blot Analysis

Production and subsequent detection of proteins in shake flask fermentations depends upon several factors such as: yeast strain selection, which is empirical, the growth conditions of transformants, induction regimen, susceptibility of proteins to proteases, and the specificity of antibodies used for protein detection on western blots. Certain antibodies seemed to be more susceptible to degradation and thus sample collection time was optimized for each antibody.

The fermentation was carried out in 200 ml media using standard conditions. The yeast strains used in the experiments could only reach 4–5 OD in most experiments under standard conditions. The expression of ApoH and ApoL chains of NRX-1 was obtained by galactose induction of yeast transformants. The presence of ApoH and ApoL chains in cell extracts and supernatant was demonstrated by western blot analysis. When single plasmids were used for expression, ApoL chain migrated with its expected molecular weight (FIG. 3, lane 6) but the ApoH chain (FIG. 3, lane 9) was found to be less stable and only seen in some of the yeast strains. When both plasmids were used for cotransformation in a single yeast strain, this contransformant produced equivalent amounts of both ApoH and ApoL chains (FIG. 3, lane 11). NRX-1 antibody provided by NeoRx (Seattle, Wash.) was used as a positive control (FIG. 3, lane 1). No detectable bands were seen in the negative control (FIG. 3, lane 7), yeast strain transformed with pPM40 (Motwani et al., *Protein Expression and Purification* 8:477 (1996)). In some yeast strains (Y112 and Y113), higher expression of antibody chains were seen in cell lysates (FIG. 4, lane 9) compared to the one in supernatant (see Example 5 and FIG. 4, lane 4).

High levels of secretion of two bands was obtained from the Y113 cotransformed with two plasmids for NRX-1 antibody (FIG. 5). This supernatant was concentrated to 20x and unreduced sample was run on gel with positive antibody control. Protein bands were found which migrate at the same levels as unreduced NRX-1 antibody molecule (FIG. 5, lane 1=purified NRX-1, lane 4=yeast expressed NRX-1). A further reduction of this sample showed two bands which migrated to expected mol. wt of ApoH and ApoL chains (FIG. 5, lane 4). High levels of antibody chains had to be produced to detect fully assembled molecule migrating at 150 kd on reducing gels (FIG. 5, lane 4).

Example 5
Expression of Fusion Protein, ScFv-SA+Fab-SA
A. Construction of the ScFv-SA Expression Plasmid The nucleic acid encoding fusion protein consisting of a single chain Fv of NRX1 fused to the amino terminal end of streptavidin (SA), designated ScFv-SA was obtained from NeoRx (Seattle, Wash.). The nucleic acid encoding a single-chain Fv/streptavidin fusion protein was cloned into the expression cassette of the present invention. The expression cassette was subcloned into a high copy yeast vector, pPM40 (FIG. 6), and transformed into various *S. cerevisiae* strains.

B. ScFv-SA Protein Expression

The transformed yeast were grown and samples were analyzed by SDS-PAGE electrophoresis (FIG. 7A) and native gel electrophoresis (FIG. 7B). Samples were collected at 24 hours (FIGS. 7A and B lanes 2 and 3), 36 hours (FIGS. 7A and B, lanes 5 and 6) and 72 hours (FIGS. 7A and B, lanes 8 and 9). In the gels, T=tetramer and M=monomer. Western blots of reducing gel-resolved proteins from shake flask fermentations were carried out by standard techniques and detected anti-streptavidin antibody reactive bands migrating in the molecular weight range of 64 kDa, corresponding to the correct dimeric form (D) of ScFv-SA (FIG. 7A, lanes 2, 3, 5, 6, 8 and 9). Immunoblots of the same samples run on native gels revealed a band at 172 kDa (FIG. 7B, lanes 2, 3, 5, 6, 8 and 9). The size of this detected band corresponds to the predicted tetrameric form (T) of the ScFv-SA protein, as the native, functional form of streptavidin is a tetramer. Control lanes 4, 7 and 10 were supernatants from yeast transformed with plasmid alone. More than 90% of the recombinant protein was secreted into the medium. The fusion protein was not detected in the cellular lysates. The ScFv-SA produced by the Yeast expression system of the present invention was compared to purified ScFv-SA produced in bacteria by SDS-PAGE gel electrophoresis and western blot analysis using antistreptavidin antibody was performed using standard techniques. FIG. 4, lanes 2 and 3 show bacterial produced ScFv-SA and lanes 3–7 show the ScFv-SA produced by the yeast expression system of the present invention.

The immunoblot in FIG. 8 compares the ScFv-SA produced in crude form from yeast (lanes 6 and 7, 2 liter fermentation) with the purified form of the same protein that was expressed in *E. coli* (lanes 2 and 3). Antistreptavidin-reactive bands were not detected in sample from the control plasmid fermentation (lane 8). Putative tetrameric (T) and dimeric (D) forms of ScFv-SA were detected as shown by arrowheads. The ScFv-SA produced in the yeast expression system of the present invention was qualitatively similar to the corresponding protein produced in *E. coli*. However, the ScFv-SA produced in *E. coli* contained less dimeric form due to the removal of the dimeric form during purification.

C. Functional Antigen Binding Assay for ScFv-SA

Antigen binding specificity was shown using crude secreted protein from yeast fermentation to detect purified recombinant EGP-2 protein in immunoblots, as ScFv is an anti-EGP-2 antibody. Various concentrations of EGP-2 were analyzed by SDS-PAGE gel electrophoresis, transferred to nitrocellulose, and subject to western blot analysis using ScFv-SA using standard techniques. FIG. 9 shows the ability of ScFv-SA produced by the present invention to detect EGP-2 (panel 1), (panel 2=purified *E. coli* produced ScFv-SA as positive control, panel 3=negative control supernatant used in western blot). The results indicate that the ScFv-SA fusion protein expressed in *S. cerevisiae* using the yeast expression system of the present invention maintained antigen binding activity.

D. Quantitation of Expression of ScFv-SA

To quantitate the relative amount of ScFv-SA produced by the yeast expression system of the present invention, ELISA plates (VWR, Plainfield, N.J.) were coated with 1 μg/ml biotinylated ScFv-SA. Serial dilutions of either the *E. coli* produced ScFv-SA (FIG. 10, rows 1–6) or the ScFv-SA produced by the yeast expression system of the present invention (supernatant of yeast transformed with a vector expressing ScFv-SA, FIG. 10, rows 7–11) were incubated with the biotinylated protein. Biotin-bound streptavidin of the ScFv-SA was detected using a horseradish peroxidase-conjugated antibody to streptavidin and ABTS colorimetric substrate by the protocol provided by the supplier (Sigma, St. Louis, Mo.). Quantitation was determined using an automatic plate reader/spectrophotometer (Dynatech, Alexandria, Va.) at 410 nm with a 490 nm reference. FIG. 10 shows the results of the ELISA quantitation assay. It was calculated that 10–20 mg/L of secreted biotin reactive fusion protein was produced using the yeast expression system of the present invention. Since only the supernatant was analyzed, it is likely that the yeast host cells may also contain expressed ScFv-SA. Therefore, the actual fusion protein yields may be much higher.

Example 6

Production of the Two-chain Fab-SA Fusion Protein

A. Construction of the Fab-SA Expression Plasmid

The nucleic acid sequences encoding the two chains the Fab-SA fusion protein (immunoglobin light chain ($V_L$) and the heavy chain ($V_H$) fused to a streptavidin gene) were obtained from the plasmid A173B-3 (NeoRx, Seattle, Wash.). The nucleic acid sequences were cloned separately into yeast expression cassettes in universal plasmids (FIG. 1) wherein a first expression cassette comprises a nucleic acid encoding the heavy chain and a second expression cassette comprises a nucleic acid encoding the light chain. Both expression cassettes were subsequently cloned into a single high copy yeast vector, pPM40 (FIG. 2 and FIG. 11), and transformed into various *S. cerevisiae* strains.

B. Fab-SA Protein Expression

*S. cerevisiae* was transformed with the Fab-SA expression plasmid of FIG. 11 and were grown and induced as described above in Example 4. Fermentation supernatant samples (48 hours after induction) were analyzed by SDS-PAGE electrophoresis (FIG. 12, lanes 2–4). Supernatant from control plasmid transformants was included as a negative control (lane 5). In the figures, Fd=$V_H$/streptavidin fusion protein, and $V_L$=light chain variable region peptide. Western blots of reducing gel-resolved proteins from shake flask fermentations were carried out by standard techniques and proteins were detected using either anti-streptavidin/horseradish peroxidase (HRP) or anti-light chain IgG/HRP conjugated antibodies, which reacted with bands migrating in the molecular weight range of 64 kDa and 32 kDa, corresponding to the correct Fd chain and $V_L$ chains of Fab-SA, respectively. More than 90% of the recombinant protein produced by the yeast expression system of the present invention was secreted into the medium.

Figure 13:
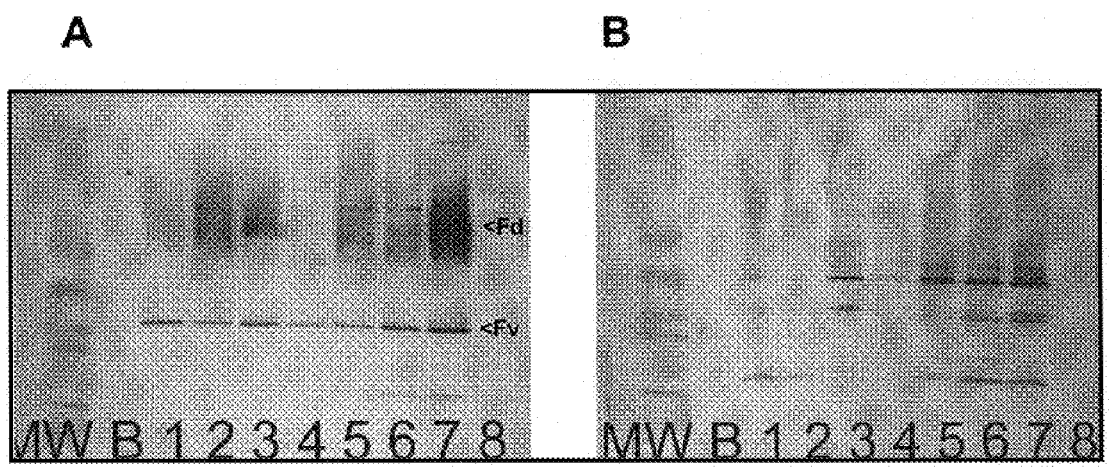

In addition, the Fab-SA expression plasmid was transformed into multiple *S. cerevisiae* strains and tested for optimal expression level and functionality of the immunoglobin/fusion chains. FIG. 13 shows immunoblots of fermentation supernatants (panel A) and the corresponding cellular lysates (panel B) from seven of these transformant strains that express Fab-SA. These strains are Y124, Y125, Y112, Y116, Y114, Y113, Y120 (lanes 1–7 respectively). Strain Y116 transformed with vector alone was included as a negative control (lane 8). Positions of the light chain variable region (Fv) and heavy chain variable/streptavidin fusion (Fd) bands are indicated by arrows. Differential expression levels of the two Fab-SA chains were obtained from the various yeast strains. All strains tested exhibited expression of the light (Fv) chain. However, only strains Y112, Y120 (lanes 3 and 7 respectively) and Y116 produced significant levels of both the Fv and Fd chains. Highest expression levels were obtained from strain Y120 (lane 7).

C. Quantitation of Expression of Fab-SA

Relative quantitation of Fab-SA in various yeast strains was determined by detection of binding to biotinylated protein in an ELISA assay (FIG. 14) as described above in Example 5D for FIG. 10. Serial dilutions of the *E. coli* produced ScFv-SA (rows 1–6) or supernatant samples from the yeast strains Y113, Y117, Y118, Y119, Y120 (rows 8–12 respectively) expressing Fab-SA by the yeast expression system of the present invention were incubated with biotinylated protein bound to ELISA plate wells. Colorimetric detection of biotin-bound recombinant protein was used to estimate relative yield. It was calculated that at least 10–20 mg/L of secreted biotin reactive fusion protein was produced by all yeast strains shown using the yeast expression system of the present invention in small-scale fermentations. Since only the supernatant was analyzed by this assay, it is likely that the yeast host cells may also contain expressed ScFv-SA. Therefore, the actual fusion protein yields may be higher.

Example 7

Production of Glucose Oxidase Immunotoxin

A Prototype Antibody Gene

The *E. coli* expression vector, pSPORT-FvSA1 was obtained from NeoRx (Seattle, Wash.). This vector contains the combined single-chain variable region sequences of an EGP-2-specific monoclonal antibody fused to a streptavidin gene (Breitz et al., *Nucl. Med.* 33:1099 (1992)) in a contiguous reading frame, cloned into the pSPORT plasmid (Life Technologies, Gaithersburg, Md.).

B. Glucose Oxidase Gene

The glucose oxidase gene sequences to be used for immunotoxin construction have been isolated and characterized. Whittington et al., *Curr. Genet.* 18:531 (1990). A genomic clone from *A. niger* contains the entire GO coding region, consisting of a single exon. It has been determined that a 22 amino acid hydrophobic signal sequence precedes the mature peptide-coding region.

C. Construction of the Immunotoxin ScFv-GO Fusion Gene and Expression Cassette

The Fv region of pSPORT-FvSA template was amplified by polymerase chain reaction (PCR) using oligonucleotide primers which introduced a 5' Eco RI restriction site, and a 3' Bam HI site into the PCR product. The glucose oxidase coding region (beginning with the first codon of the mature peptide) was obtained by PCR using a plasmid template containing a genomic insert from *A. niger* and primers which incorporated a 5' Bam HI site, and a 3' Not I site (Life Technologies, Rockville, Md.) into the amplified sequences. The FvSA and GO fragments were cloned by three-way ligation into a pBluescript plasmid (Stratagene, La Jolla Calif.) containing the yeast expression cassette described above. Eco RI and Not I restriction sites located between the secretory and termination sequences were utilized to insert the immunotoxin components in frame. The resultant plasmid is(SK+[GO Fusion]). The complete expression cassette was removed from this plasmid via restriction digestion with KpnI and SphI, and cloned by blunt-end ligation into either or both of the unique BamHI and HpaI sites in the pPM40 yeast shuttle vector (FIG. 15). A single expression cassette, or multiple expression cassettes were cloned into the yeast shuttle vector. The DNA from this plasmid was transformed into several yeast strains and fermentation was carried out by standard techniques known in the art.

D. Analysis of Recombinant ScFv-GO Fusion Proteins by Western Blot Analysis

The culture supernatants were concentrated with Centricon 30 filters by ultrafiltration and used for SDS-PAGE analysis. Cell pellets (2 OD) were lysed directly in reducing sample buffer (1.5% w/v SDS, 2.5% v/v bromophenol blue, 5% v/v glycerol, 2.5% 2-mercaptoethanol) and boiled at 95° C. for 5 minutes prior to electrophoretic separation. If degradation of proteins was observed, 0.5 mM PMSF was included in the buffer. Samples were resolved on tris-glycine gradient gels (4–20% acrylamide). Molecular weight markers and precast gels were obtained from Novex (San Diego, Calif.). FIG. 16 shows the results of SDS-PAGE gel electrophoresis followed by western blot analysis with anti-glucose oxidase antibody. Lane 1 contains the supernatant of a yeast transformed with a negative control plasmid (no expression cassette), Lanes 2 and 3 contain the supernatant of a yeast transformed with a vector comprising the expression cassette encoding ScFv-GO (FIG. 15). A band migrating at approximately 140 KD is indicated with an arrow which corresponds to a tetrameric ScFv-GO fusion protein.

E. ScFv-GO Fusion Protein Quantitation

Total protein from fermentation supernatants and cell lysates was quantitated using the BCA Protein Assay System (Pierce, Rockford Ill.). Commercially purified bovine serum albumin was used to establish concentration standards. Detection and quantitation of specific peptides was determined using the ECL Chemiluminescent Western Blotting System (Amersham, Piscataway, N.J.). Detected bands of samples and standards were recorded by densitometric scan and relative quantitation determined using the Scion Image program (Scion, Md.). Plasmids containing either single or multiple expression cassettes yielded an average of 20–40 mg/L in shake flask fermentations.

Example 8

Testing of the Immunotoxin for Functionality

A. Functional (Antigen Binding) Assay of the GO-immunotoxin

Detection of functional immunotoxin binding to Western blots of purified EGP-2 antigen was performed as described above in Example 5 above for the ScFv-SA expressed protein. FIG. 17, panel 2 (ApoLife ScFv-GO) shows that the ScFv-GO produced by the yeast expression system of the present system was able to bind EGP-2 as was control ScFv-GO produced in *E. coli* (panel 1, positive control). Supernatant from negative control fermentations did not bind antigen (panel 3, negative control).

B. ELISA

Purified glucose oxidase protein (Sigma, St. Louis, Mo.) was added at various concentrations to generate a standard curve. Following 5 washes (phosphate buffered saline [PBS], 0.5% Tween 20), glucose oxidase specific antibody (sheep anti-GO, #AB1221, Chemicon, Temeula, Calif.) was incubated for 1 hour at room temperature (RT), followed by washes and a 1 hour incubation with horseradish peroxidase conjugated anti-sheep antibody (diluted 1:2000, Zymed, San Francisco, Calif.). After washing, the samples were quantitated by comparison to standard curve data generated by first order, log x/log y regression analysis.

C. Detection and Quantitation of Glucose Oxidase Activity

Two methods of quantitating glucose oxidase activity were employed. The first method has been described previously (Wittington et al., *Curr. Genet.* 18:531 (1990). FIG. 18 shows an example using this assay. Fermentation samples of transformed yeast containing an ScFv-GO expression plasmid were harvested at various time points post-induction and concentrated 20-fold by ultrafiltration. A 10 $\mu$l aliquot of each sample was assayed for glucose oxidase activity. Purified glucose oxidase protein at various concentrations was also assayed in parallel (A3–A5). Additional controls included reagents alone (A1), PBS (A2) and pPM40 fermentation sample (vector alone, B5). The presence of hydrogen peroxide, indicative of glucose oxidase activity, was detected in B2–B4 fermentation samples expressing ScFv-GO whereas the control fermentation (pPM40, B5) contained no detectable hydrogen peroxide. An estimated 1000 units/L was obtained. Varying the pH of the fermentation may improve this yield of activity since the activity of the glucose oxidase enzyme is pH dependant.

The second method employed for detecting glucose oxidase activity was the Amplex Red Hydrogen Peroxide Assay Kit (Cat. # A-12212, Molecular Probes, Eugene, Oreg.) as per manufacturers suggested protocols. This highly sensitive assay detects hydrogen peroxide ($H_2O_2$) by its conversion of the Amplex Red (10-acetyl-3,7-dihydroxyphenoxazine) reagent in the presence of horseradish peroxidase to produce a highly fluorescent and stable product, resorufin. Peroxide production is initiated by the addition of glucose to the reaction mixture containing the recombinant immunotoxin. The fluorescence generated by the reaction was detected by using a fluorimeter set for excitation in the range of 530–560 nm and emission detection at 590 nm. FIG. 18 shows the ability of control GO (Panel A, rows 3–5, 0.25 Units/ml GO, 0.5 U/ml and 1.0 U/ml respectively) and ScFv-GO produced by the yeast expression system of the present invention (Panel B, rows 3 and 4, 24 hour and 48 hour post-induction) to produced $H_2O_2$. Data from peroxide generation assay is combined with specific protein levels detection to determine specific activity (units/g protein) and concentration (units/liter).

D. Glycosylation of ScFv-GO

FIG. 19 compares the ScFv-GO from crude fermentation supernatants with endoglycosidase H treatment (lane 1) and without endoglycosidase H treatment (lane 3) to detect the presence of N-linked glycosylation residues added to the recombinant protein, since it has been reported that N-linked glycosylation is essential to the function of glucose oxidase. See Whittington et al., *Curr. Genet.* 18:531 (1990); Frederick et al., *J. Biol. Chem.* 265:3793 (1990). 20 $\mu$l of crude fermentation supernatant from ScFv-GO production was treated with 10 units of endoglycosidase H (Boehringer Mannheim, Indianapolis, Ind.) at 37° C. for 16 hours prior to being resolved by SDS-PAGE electrophoresis. Endoglycosidase H treatment (lane 2) results in a band that migrates at a lower molecular weight and which has a more distinct banding pattern than the untreated sample (lane 1). Therefore, significant N-linked glycosylation is present on the yeast-secreted form of ScFv-GO, indicative of correct post-translational processing in the yeast expression system of the present invention. By comparison, treatment of ScFv-SA (lanes 3, untreated and lane 4, endoglycosidase H treated) did not result in a shift in specific bands, indicating that N-linked glycosylation is not present in this fusion protein.

E. Comparison of ScFv-GO Expression in Various Yeast Strains

FIG. 20 shows the western blot analysis of ScFv-GO immunotoxin expressed in the fermentation supernatant of various transformed *S. cerevisiae* yeast strains. The yeast strains which were employed are as follows: Y111, Y124, Y125, Y112, Y116, Y114 and Y120 (lanes 1–7, respectively). Supernatant samples were harvested at 24 hours post-induction. These data demonstrate that (1) Y111 did not express the GO-fusion protein, lane 1; (2) strains Y124 and Y125, lanes 2 and 3, respectively, expressed small amounts of the fusion protein which may be non-glycosylated; (3) Y112, lane 4, a protease deficient strain, expressed the putative unglycosylated form of ScFv-GO; (4) Y116 and Y114, lanes 5 and 6, respectively, expressed the glycosylated form of the ScFv-GO protein; and (5) Y120, lane 7, expressed the glycosylated form of the ScFv-GO protein in the highest levels.

Example 9
Comparison of Different Media for the Growth of Yeast Strains

FIG. 21 shows the relative growth, in terms of optical density, obtained after fermentation of yeast strain Y113 (designated as RgsApoFGt (ScFv-SA) in the figure) in the various media compositions as shown. The yeast was transformed with either the ScFv-SA fusion protein expression vector (see Example 5) or with vector alone (pPM40) as a control. Optimal yeast cell growth was obtained in minimal salt medium (MSM) (Methods in Yeast Genetics. Cold Spring Harbor Laboratory, Cold Spring Harbor, N.Y. (1986)) supplemented with additional biotin for both fusion protein expressing and non-expressing yeast transformants.

Various publications are cited herein, the contents of which are hereby incorporated by reference in their entireties.

We claim:

1. A vector comprising a first and second expression cassette wherein the first expression cassette includes a nucleic acid encoding a heterologous recombinant fusion protein which comprises an immunological molecule and a toxin wherein the immunological molecule is a first chain of an immunological molecule and the toxin is glucose oxidase, and the second expression cassette includes a nucleic acid encoding a heterologous recombinant fusion protein which comprises an immunological molecule and a toxin wherein the immunological molecule is a second chain of an immunological molecule and the toxin is horseradish peroxidase.

2. The vector of claim 1 wherein said first chain is heavy chain and said second chain is light chain.

3. The vector of claim 1 wherein said first chain is light chain and said second chain is heavy chain.

* * * * *

UNITED STATES PATENT AND TRADEMARK OFFICE
CERTIFICATE OF CORRECTION

PATENT NO. : 6,358,733 B1
DATED : March 19, 2002
INVENTOR(S) : Motwani et al.

It is certified that error appears in the above-identified patent and that said Letters Patent is hereby corrected as shown below:

Drawings,
Sheet 9 of 22, please replace the image in Figure 9 with the following image:

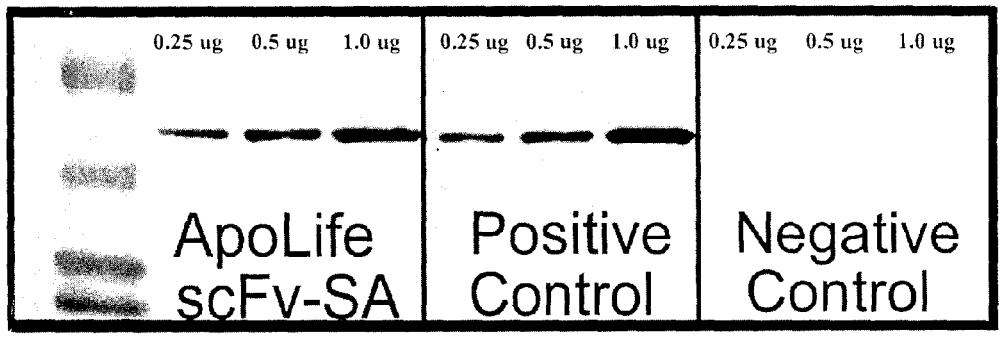

Sheet 12 of 22, please replace the image in Figure 12 with the following image:

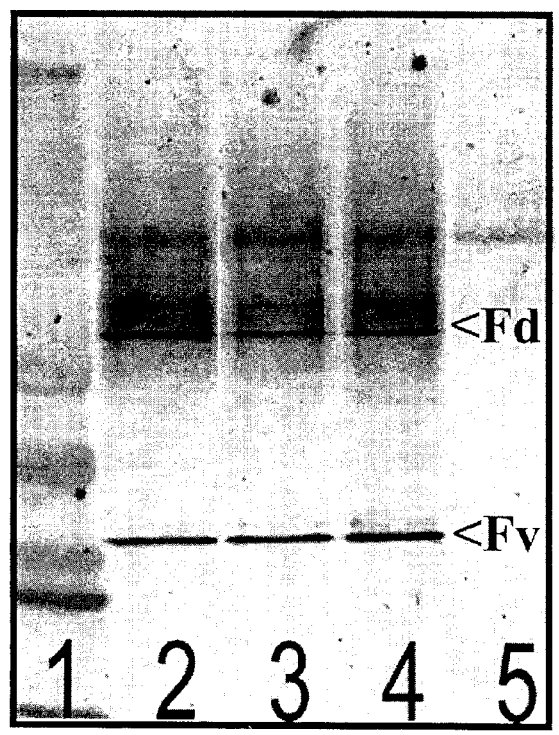

UNITED STATES PATENT AND TRADEMARK OFFICE
CERTIFICATE OF CORRECTION

PATENT NO.    : 6,358,733 B1
DATED         : March 19, 2002
INVENTOR(S)   : Motwani et al.

It is certified that error appears in the above-identified patent and that said Letters Patent is hereby corrected as shown below:

Column 9,
Line 25, please replace the term "NSBI" with the term -- SBIR --

Column 22,
Line 15, please delete the sentence "In the gels, T=tetramer and M=monomer"
Line 34-37, please delete the sentence " FIG.4, lanes 2 and 3 show bacterial produced scFv-SA and lanes 3-7 show the scFv-SA produced by the yeast expression system of the present invention."

Figure 18:
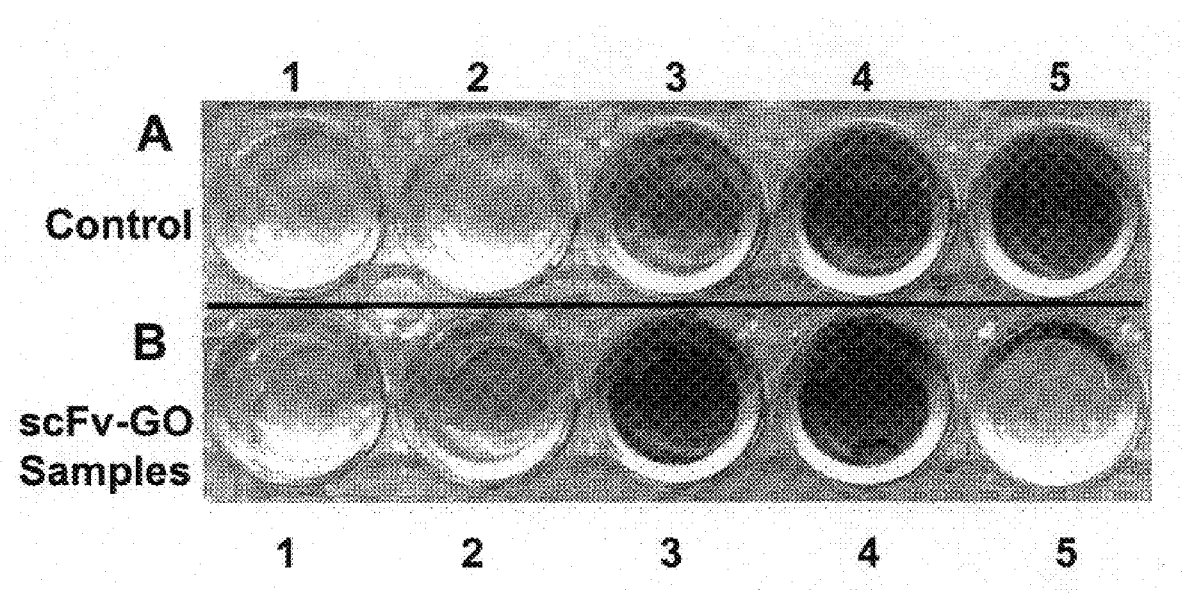

Column 26,
Lines 27-32, please delete the sentence "FIG. 18 shows the abiliy of control GO (Panel A, rows 3-5, 0.25 Units/ml GP, 0.5 U/ml and 1.0 U/ml respectively) and ScFv-GO produced by the yeast expression system of the present invention (Panel B, rows 3 and 4, 24 hour and 48 hour post-induction) to produce $H_2O_2$."

Signed and Sealed this

Fifteenth Day of April, 2003

JAMES E. ROGAN
*Director of the United States Patent and Trademark Office*